US008354109B2

(12) United States Patent
Hogarth et al.

(10) Patent No.: US 8,354,109 B2
(45) Date of Patent: Jan. 15, 2013

(54) MULTIMERIC FC RECEPTOR POLYPEPTIDES

(75) Inventors: Phillip Mark Hogarth, Williamstown (AU); Bruce David Wines, Heidelberg (AU)

(73) Assignee: Suppremol GmbH, Martinsried (DE)

( * ) Notice: Subject to any disclaimer, the term of this patent is extended or adjusted under 35 U.S.C. 154(b) by 576 days.

(21) Appl. No.: 11/762,664

(22) Filed: Jun. 13, 2007

(65) Prior Publication Data
US 2008/0008700 A1 Jan. 10, 2008

Related U.S. Application Data

(63) Continuation-in-part of application No. PCT/AU2006/001890, filed on Dec. 13, 2006.

(60) Provisional application No. 60/750,301, filed on Dec. 13, 2005.

(51) Int. Cl.
*A61K 39/00* (2006.01)
(52) U.S. Cl. .......... 424/184.1; 424/192.1; 424/810; 514/15.4; 514/16.6; 530/350; 530/868
(58) Field of Classification Search .......... None
See application file for complete search history.

(56) References Cited

U.S. PATENT DOCUMENTS

| | | | | |
|---|---|---|---|---|
| 6,355,683 | B1 * | 3/2002 | Baell et al. | 514/568 |
| 7,332,631 | B2 * | 2/2008 | Hogarth et al. | 568/42 |
| 7,700,100 | B2 * | 4/2010 | Johnson et al. | 424/134.1 |
| 7,714,104 | B2 * | 5/2010 | Bodie et al. | 530/327 |
| 2003/0195338 | A1 | 10/2003 | Chung et al. | |

FOREIGN PATENT DOCUMENTS

| WO | WO 91/06570 | 5/1991 |
|---|---|---|
| WO | WO 2004/062619 | 7/2004 |
| WO | WO 2005086947 A2 * | 9/2005 |

OTHER PUBLICATIONS

Bournazos et al., Clin Exp Immunol, 2009, 157:244-254.*
Raghavan et al., Annu. Rev. Cell Dev. Biol. 1996, 12:181-220.*
Kurucz et al., "Baterially expressed human FcgammaRIIB is soluble and functionally active after in vitro refolding" Immunology Letters, vol. 75, No. 1, Dec. 1, 2000, pp. 33-40.
Powell, et al., "Investigation of FcgammaRIIa dimerization", FASEB Journal, vol. 14, No. 6, Apr. 20, 2000, p. A960.
Supplementary European Search Report for International Application No. EP06828004, completed Jan. 22, 2009.
Powell et al., Alteration of the FcγRIIa Dimer Interface Affects Receptor Signaling but Not Ligand Binding, The Journal of Immunology 176 (12): 7489-7494, 2006.
Li et al., Recombinant CD16A-Ig forms a homodimer and cross-blocks the ligand binding functions of neutrophil and monocyte Fcγ receptors, Molecular Immunology 38, 527-538, 2001.
Maxwell et al., Crystal structure of the human leukocyte Fc receptor, FcγRIIa, Nature Structural Biology 6(5), 437-442, 1999.
Harrison et al., High affinity IgG binding by FcγRI (CD64) is modulated by two distinct IgSF domains and the transmembrane domain of the receptor, Protein Engineering 11(3), 225-232, 1998.
Kershaw et al., Redirected Cytotoxic Effector Function, The Journal of Biological Chemistry 271(35), 21214-21220, 1996.
Hulett et al., Multiple Regions of Human FcγRII (CD32) Contribute to the Binding of IgG, The Journal of Biological Chemistry 270(36), 21188-21194, 1995.
Ierino et al., Recombinant soluble human Fc gamma RII: production, characterization, and inhibition of the Arthus reaction, Journal of Experimental Medicine178(5):1617-28, 1993.
International Search report for PCT/AU2006/001890, mailed Feb. 28, 2007.
Francesco L. Ierino et al.; "Mapping Epitopes of Human FCγRII (CDW32) With Monoclonal Antibodies and Recombinant Receptors1"; vol. 150, 1794-1803, No. 5, Mar. 1, 1993.
Kathryn L. Armour et al.; "Differential Binding to Human FCγRIIA and FCYRIIB Receptors by Human IGG Wildtype and Mutant Antibodies"; Molecular Immunology; 40 (2003) 585-593.
Anne Astier et al.; "Human Epidermal Langerhans Cells Secrete a Soluble Receptor for IGC (FCγRII/CD32) That Inhibits the Binding of Immune Complexes to FCYR+ Cells1"; Journal of Immunology, 1994, 152:201.
P. Emery et al.; "Who Collaborating Centre Consensus Meeting on Anti-Cytokine Therapy in Rheumatoid Arthritis"; Rheumatology 2001; 40:699-702.
Mark J. Evans et al.; "Rapid Expression of an Anti-Human C5 Chimeric Fab Utilizing a Vector That Replicates in COS and 293 Cells"; Journal of Immunological Methods 184 (1995) 123-138.
Scott C. Garman et al.; "Structure of the FC Fragment of Human IGE Bound to its High-Affinity Receptor FCεRL"; Nature; vol. 406, Jul. 20, 2000v.
Andrew B. Herr et al.; "Insights Into IGA-Mediated Immune Responses From the Crystal Structures of Human FCARI and its Complex With IGA1-FC"; Nature; vol. 423, Jun. 5, 2003.
Mark D. Hulett et al.; "Chimeric FC Receptors Identify Functional Domains of the Murine High Affinity Receptors for IGG1"; vol. 147, 1863-1868, Sep. 15, 1991.
Mark D. Hulett et al.; "The Second and Third Extracellular Domains of FCΓRI (CD64) Confer the Unique High Affinity Binding of IGG2A"; Molecular Immunology 35 (1998) 989-996.
Maenaka et al.; "The Human Low Affinity FCY Receptors IIa, IIb, and III Bind IgC With Fast Kinetics and Distinct Thermodynamic Properties"; The Journal of Biological Chemisty; vol. 276, No. 48, Issue of Nov. 30, pp. 44898-44904, 2001.
Indik et al.; "Blood"; The Journal of the American Society of Hematology; vol. 86, No. 12, Dec. 15, 1995; pp. 4389-4399.

(Continued)

*Primary Examiner* — Michael Szperka
(74) *Attorney, Agent, or Firm* — Baker Donelson Bearman, Caldwell & Berkowitz, PC

(57) ABSTRACT

A soluble multimeric protein or polypeptide is disclosed that is able to inhibit interaction of leukocyte Fcγ receptors (FcγR) and immunoglobulin G (IgG). The protein or polypeptide comprises two or more linked Fc binding regions, at least one of which is derived from an FcγR type receptor and, particularly, FcγRIIa. Also described are polynucleotide molecules encoding the protein or polypeptide and the use thereof in methods of treating a subject for an immune-complex (IC)-mediated inflammatory disease.

8 Claims, 25 Drawing Sheets

OTHER PUBLICATIONS

Nakamura et al.; "FC Receptor Targeting in the Treatment of Allergy, Autoimmune Diseases and Cancer"; Expert Opin. Ther. Targets (2005) 9(1):169-190.

Wines et al.; The Interaction of FCαRI With IgA and its Implication for Ligand Binding by Immunoreceptors of the Leukocyte Receptor Cluster1; The Journal of Immunology, 2001, 166:1781-1789.

Maxwell et al.; "Crystal Structure of the Human Leukocyte FC Receptor, FCγRIIA"; Nature Structural Biology; vol. 6, No. 5, May 1999.

Pflum et al.; "The Arthus Reaction in Rats, a Possible Test for Anti-Inflammatory and Antirheumatic Drugs"; Agents and Action; vol. 9/2 (1979).

Powell et al.; "Biochemical Analysis and Crystallisation of FCγRIIA, the Low Affinity Receptor for IGG"; Immunology Letters 68 (1999) 17-23.

Sondermann et al.; "The 3.2-Å Crystal Structure of the Human IGG1 FC Fragment-FCγRIII Complex"; Nature; vol. 406, Jul. 20, 2000.

Sondermann et al.; "Molecular Basis for Immune Complex Recognition: A Comparison of FC-Receptor Structures"; J. Mol. Biol. (2001) 309, 737-749.

Takai; "Roles of FC Receptors in Autoimmunity"; Nature; vol. 2, pp. 580-592; Aug. 2002.

Wines et al.; "Enhancement of the Binding of C1Q to Immune Complexes by Polyethylene Glycol"; Molecular Immunology, vol. 25, No. 3, pp. 263-266, 1988.

Seki; "Identification of Multiple Isoforms of the Low-Affinity Human IGG FC Receptor"; Immunogenetics 30: 5-12, 1989.

Carron et al., "Thrombolysis for massive pulmonary tumor embolism in a patient with cavoatrial renal carcinoma," British J. Anesthesia, 1010(2): 285-286 (Aug. 2008).

Malm et al., "Successful Thrombolysis of an Occluded Modified Blalock Shunt Three Days After Operation," The Annals of Thoracic Surgery, 1998, p. 1453-1455, The Society of Thoracic Surgeons.

Janeway et al., "Janeway's immunoblology", 7th ed., Garland Science, New York; p. 410, Fig. 9.30, 2008.

* cited by examiner

```
                    -31-30                                 -20
       atggagacccaaatgtctcagaatgtatgtcccagaaacctgtggctgcttcaaccattg
        M   E   T   Q   M   S   Q   N   V   C   P   R   N   L   W   L   L   Q   P   L
                -10                                  -1 +1
       acagttttgctgctgctggcttctgcagacagtcaagctgcagctcccccaaaggctgtg
        T   V   L   L   L   A   S   A   D   S   Q   A   A   A   P   P   K   A   V
       10                       20
       ctgaaacttgagcccccgtggatcaacgtgctccaggaggactctgtgactctgacatgc
        L   K   L   E   P   P   W   I   N   V   L   Q   E   D   S   V   T   L   T   C
       30                       40
       caggggctcgcagccctgagagcgactccattcagtggttccacaatgggaatctcatt
        Q   G   A   R   S   P   E   S   D   S   I   Q   W   F   H   N   G   N   L   I
       50                       60
       cccacccacacgcagcccagctacaggttcaaggccaacaacaatgacagcggggagtac
        P   T   H   T   Q   P   S   Y   R   F   K   A   N   N   N   D   S   G   E   Y
       70                       80
       acgtgccagactggccagaccagcctcagcgaccctgtgcatctgactgtgctttccgaa
        T   C   Q   T   G   Q   T   S   L   S   D   P   V   H   L   T   V   L   S   E
       90                       100
       tggctggtgctccagacccctcacctggagttccaggagggagaaaccatcatgctgagg
        W   L   V   L   Q   T   P   H   L   E   F   Q   E   G   E   T   I   M   L   R
       110                      120
       tgccacagctggaaggacaagcctctggtcaaggtcacattcttccagaatggaaaatcc
        C   H   S   W   K   D   K   P   L   V   K   V   T   F   F   Q   N   G   K   S
       130                      140
       cagaaattctcccattt<u>GGATCC</u>cacctctccatcccacaagcaaaccacagtcacagt
        Q   K   F   S   H   L   D   P   T   F   S   I   P   Q   A   N   H   S   H   S
       150                      160
       ggtgattaccactgcacaggaaacataggctacacgctgttctcatccaagcctgtgacc
        G   D   Y   H   C   T   G   N   I   G   Y   T   L   F   S   S   K   P   V   T
       170                      180
       atcactgtccaagtgcccagcatgggcagctcttcacccgtagctcccccaaaggctgtg
        I   T   V   Q   V   P   S   M   G   S   S   S   P   <u>V</u>   A   P   P   K   A   V
       190                      200
       ctgaaacttgagcccccgtggatcaacgtgctccaggaggactctgtgactctgacatgc
        L   K   L   E   P   P   W   I   N   V   L   Q   E   D   S   V   T   L   T   C
       210                      220
       caggggctcgcagccctgagagcgactccattcagtggttccacaatgggaatctcatt
        Q   G   A   R   S   P   E   S   D   S   I   Q   W   F   H   N   G   N   L   I
       230                      240
       cccacccacacgcagcccagctacaggttcaaggccaacaacaatgacagcggggagtac
        P   T   H   T   Q   P   S   Y   R   F   K   A   N   N   N   D   S   G   E   Y
       250                      260
       acgtgccagactggccagaccagcctcagcgaccctgtgcatctgactgtgctttccgaa
        T   C   Q   T   G   Q   T   S   L   S   D   P   V   H   L   T   V   L   S   E
       270                      280
       tggctggtgctccagacccctcacctggagttccaggagggagaaaccatcatgctgagg
        W   L   V   L   Q   T   P   H   L   E   F   Q   E   G   E   T   I   M   L   R
       290                      300
       tgccacagctggaaggacaagcctctggtcaaggtcacattcttccagaatggaaaatcc
        C   H   S   W   K   D   K   P   L   V   K   V   T   F   F   Q   N   G   K   S
       310                      320
       cagaaattctcccattt<u>GGATCC</u>cacctctccatcccacaagcaaaccacagtcacagt
        Q   K   F   S   H   L   D   P   T   F   S   I   P   Q   A   N   H   S   H   S
       330                      340
       ggtgattaccactgcacaggaaacataggctacacgctgttctcatccaagcctgtgacc
        G   D   Y   H   C   T   G   N   I   G   Y   T   L   F   S   S   K   P   V   T
       350                      360
       atcactgtccaagtgcccagcatgggcagctcttcaccctctcatcaccaccatcaccac
        I   T   V   Q   V   P   S   M   G   S   S   S   P   S   H   H   H   H   H   H
       370
       gtctag (SEQ ID NO: 5)
        V -         (SEQ ID NO: 6)
```

*Figure 1*

METQMSQNVCPRNLWLLQPLTVLLLLASADSQAAAPPKAVLKLEPPWINVLQEDSVTLTCQG
ARSPESDSIQWFHNGNLIPTHTQPSYRFKANNNDSGEYTCQTGQTSLSDPVHLTVLSEWLVL
QTPHLEFQEGETIMLRCHSWKDKPLVKVTFFQNGKSQKFSHLDPTFSIPQANHSHSGDYHCT
GNIGYTLFSSKPVTITVQVPSMGSSSPVAPPKAVLKLEPPWINVLQEDSVTLTCQGARSPESD
SIQWFHNGNLIPTHTQPSYRFKANNNDSGEYTCQTGQTSLSDPVHLTVLSEWLVLQTPHLEF
QEGETIMLRCHSWKDKPLVKVTFFQNGKSQKFSHLDPTFSIPQANHSHSGDYHCTGNIGYTL
FSSKPVTITVQVPSMGSSSPPRGPTIKPCPPCKCPAPNLEGGPSVFIFPPKIKDVLMISLSPIVT
CVVVDVSEDDPDVQISWFVNNVEVHTAQTQTHREDYNSTLRVVSALPIQHQDWMSGKAFAC
AVNNKDLPAPIERTISKPKGSVRAPQVYVLPPPEEEMTKKQVTLTCMVTDFMPEDIYVEWTN
NGKTELNYKNTEPVLDSDGSYFMYSKLRVEKKNWVERNSYSCSVVHEGLHNHHTTKSFSRT
PGK

*Figure 19* gct agc gcc acc ATG gag acc caa atg tct cag aat gta tgt ccc aga aac ctg tgg ctg ctt caa cca ttg
aca gtt ttg ctg ctg ctg gct tct gca gac agt caa gct gca gct ccc cca aag gct gtg ctg aaa ctt gag
ccc ccg tgg atc aac gtg ctc cag gag gac tct gtg act ctg aca tgc cag ggg gct cgc agc cct gag agc
gac tcc att cag tgg ttc cac aat ggg aat ctc att ccc acc cac acg cag ccc agc tac agg ttc aag gcc
aac aac aat gac agc ggg gag tac acg tgc cag act ggc cag acc agc ctc agc gac cct gtg cat ctg
act gtg ctt tcc gaa tgg ctg gtg ctc cag acc cct cac ctg gag ttc cag gag gga gaa acc atc atg ctg
agg tgc cac agc tgg aag gac aag cct ctg gtc aag gtc aca ttc ttc cag aat gga aaa tcc cag aaa ttc
tcc cat ttg gat ccc acc ttc tcc atc cca caa gca aac cac agt cac agt ggt gat tac cac tgc aca gga
aac ata ggc tac acg ctg ttc tca tcc aag cct gtg acc atc act gtc caa gtg ccc agc atg ggc agc tct
tca ccc gta gct ccc cca aag gct gtg ctg aaa ctt gag ccc ccg tgg atc aac gtg ctc cag gag gac tct
gtg act ctg aca tgc cag ggg gct cgc agc cct gag agc gac tcc att cag tgg ttc cac aat ggg aat ctc
att ccc acc cac acg cag ccc agc tac agg ttc aag gcc aac aac aat gac agc ggg gag tac acg tgc
cag act ggc cag acc agc ctc agc gac cct gtg cat ctg act gtg ctt tcc gaa tgg ctg gtg ctc cag acc
cct cac ctg gag ttc cag gag gga gaa acc atc atg ctg agg tgc cac agc tgg aag gac aag cct ctg gtc
aag gtc aca ttc ttc cag aat gga aaa tcc cag aaa ttc tcc cat ttg gat ccc acc ttc tcc atc cca caa gca
aac cac agt cac agt ggt gat tac cac tgc aca gga aac ata ggc tac acg ctg ttc tca tcc aag cct gtg
acc atc act gtc caa gtg ccc agc atg ggc agc tct tca ccc ccc aga ggg ccc aca atc aag ccc tgt cct
cca tgc aaa tgc cca gca cct aac ctc gag ggt gga cca tcc gtc ttc atc ttc cct cca aag atc aag gat
gta ctc atg atc tcc ctg agc ccc ata gtc aca tgt gtg gtg gtg gat gtg agc gag gat gac cca gat gtc
cag atc agc tgg ttt gtg aac aac gtg gaa gta cac aca gct cag aca caa acc cat aga gag gat tac
aac agt act ctc cgg gtg gtc agt gcc ctc ccc atc cag cac cag gac tgg atg agt ggc aag gca ttc gca
tgc gca gtc aac aac aaa gac ctc cca gcg ccc atc gag aga acc atc tca aaa ccc aaa ggg tca gta
aga gct cca cag gta tat gtc ttg cct cca cca gaa gaa gag atg act aag aaa cag gtc act ctg acc tgc
atg gtc aca gac ttc atg cct gaa gac att tac gtg gag tgg acc aac aac ggg aaa aca gag cta aac tac
aag aac act gaa cca gtc ctg gac tct gat ggt tct tac ttc atg tac agc aag ctg aga gtg gaa aag aag
aac tgg gtg gaa aga aat agc tac tcc tgt tca gtg gtc cac gag ggt ctg cac aat cac cac acg act aag
agc ttc tcc cgg act ccg ggt aaa tga taa ccg gtc

*Figure 20*

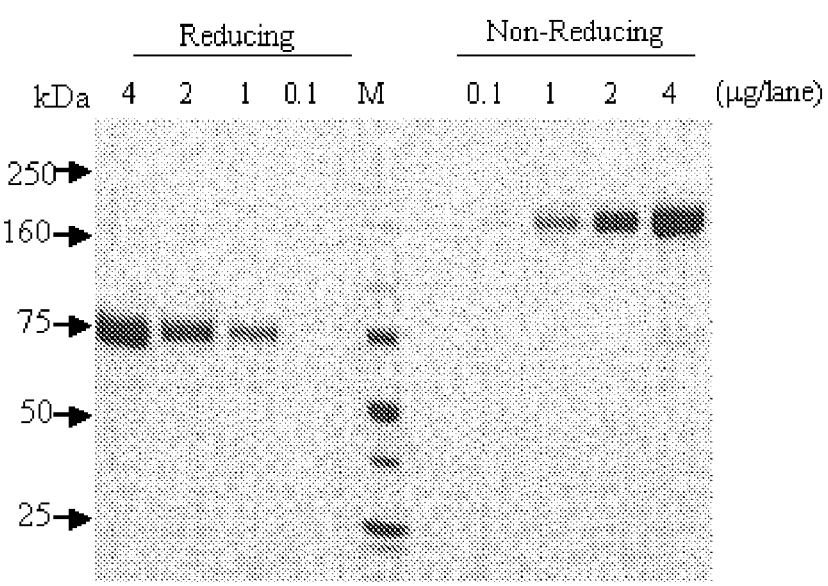
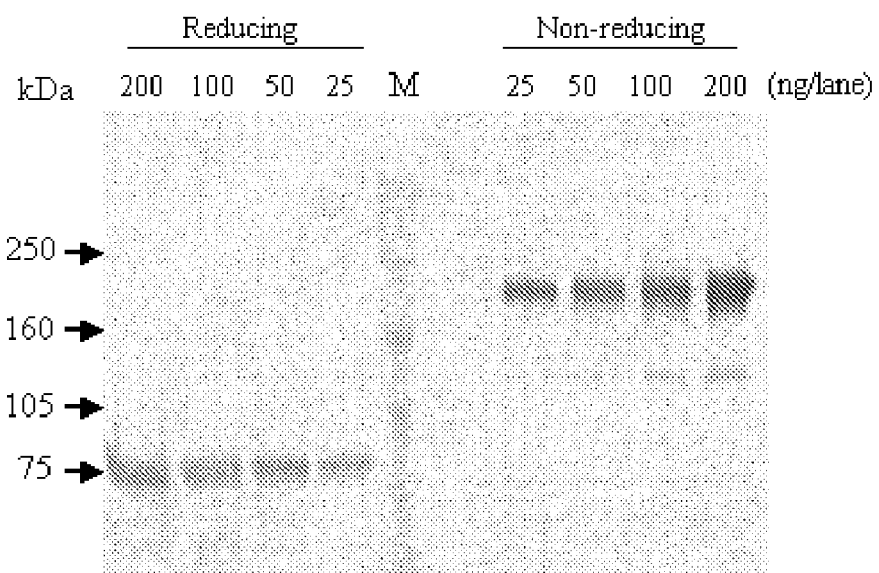
Figure 22

MULTIMERIC FC RECEPTOR POLYPEPTIDES

This application is a continuation in part of the United States designation of PCT/AU2006/001890, filed 13 Dec. 2006, which claims the benefit of priority under 35 U.S.C. §119(e) from U.S. Provisional Application Ser. No. 60/750,301, filed 13 Dec. 2005, the entire content of each which is hereby incorporated by reference in this application.

FIELD OF THE INVENTION

The present invention relates to soluble multimeric Fc receptor polypeptides able to inhibit leukocyte Fcγ receptors (FcγR) and immunoglobulin G (IgG) interactions. Such polypeptides are useful in the treatment of inflammatory diseases, particularly immune complex-mediated inflammatory diseases such as rheumatoid arthritis (RA), immune thrombocytopenic purpura (ITP) and systemic lupus erythematosus (SLE).

BACKGROUND OF THE INVENTION

The treatment of autoimmune and other inflammatory diseases such as RA and SLE has entered a new and exciting phase where increased understanding of the molecules involved in the immune system has allowed for the specific inhibition of key inflammatory molecules such as tumour necrosis factor-α(TNFα) and interleukin 1β (IL-1β). For example, in recent studies, it has been shown that antibodies can play a powerful role in the pathogenesis of RA, and in human clinical trials, positive responses to the use of anti-CD20 monoclonal antibody (MAb) therapy to eliminate antibody producing B cells have been generating strong evidence of the significant role of antibodies in RA (Emery et al., 2001). Since Fc receptors (FcR) play pivotal roles in immunoglobulin-based effector systems, inhibition of FcR function may provide the basis of effective therapy for a variety of diseases. Moreover, since Fcγ receptors (FcγR) are pivotal to effector systems for IgG, targeting the interaction between leukocyte FcγRs and antibodies provides a new opportunity for therapeutic intervention in RA (Nabbe et al., 2003). One approach of achieving such an intervention which is of interest to the present applicants is the use of a soluble form of an FcγR to act as a "decoy" to prevent leukocyte activation by antibodies.

Fc receptors (FcR) are leukocyte surface glycoproteins that specifically bind the Fc portion of antibodies. The receptors for IgG, that is FcγR, are the most widespread and diverse, the major types being FcγRI (CD64), FcγRII (CD32) and FcγRIII (CD16). Immune complexes (IC) that are formed in vivo in normal immune responses, and those seen in the pathology of autoimmune diseases such as RA, can simultaneously engage many FcR. For example, in humans, activated macrophages, neutrophils, eosinophils and mast cells can express FcγRI, FcγRIIa, FcγRIIb and FcγRIII (Takai, 2002). However, of these, the FcγRIIa is the major initiator of IC-mediated inflammation and, while all of the FcγR types engage the lower hinge region of the IgG Fc domain and the CH2 domains such that any soluble FcγR decoy polypeptide might inhibit the binding of IgG to all classes of FcγR, the present applicants have realised that since FcγRIIa shows the widest binding specificity and highest selectivity for avid IgG immune complex binding, the development and investigation of a soluble FcγRIIa offers the greatest potential.

Indeed, previous studies have shown that a simple recombinant soluble FcγRIIa polypeptide (rsFcγRIIa monomer), consisting of FcγRIIa ectodomains (Ierino et al., 1993a), is clearly able to inhibit IC-mediated inflammation. In these studies, the rsFcγRIIa was tested using the Arthus reaction, wherein immune complexes are formed in the dermis by the passive administration of antibody and antigen (Pflum et al., 1979), which is a model of vasculitis (an extra articular complication in arthritis) and also occurs in SLE. It was found that while the rsFcγRIIa monomer inhibited inflammation and neutrophil infiltration when co-administered with the antibody and antigen, large amounts of the rsFcγRIIa monomer were required because of a relatively low level of selectivity for the immune complexes. To overcome this problem, the present applicants proposed to use multimeric forms of the rsFcγRIIa decoy, and has since found, surprisingly, that not only could such multimeric forms be successfully expressed, they exhibit increased selectivity for immune complexes. Such multimeric rsFcγRIIa polypeptides therefore show considerable promise for the treatment of IC-mediated inflammatory disease such as RA and SLE.

SUMMARY OF THE INVENTION

Thus, in a first aspect, the present invention provides a soluble multimeric protein or polypeptide able to inhibit interaction of leukocyte Fcγ receptors (FcγR) and immunoglobulin G (IgG), said protein or polypeptide comprising two or more linked Fc binding regions, at least one of which is derived from an FcγR type receptor.

Preferably, the protein or polypeptide is a multimer of an Fc binding region derived from an FcγRII type receptor, particularly FcγRIIa. Such a molecule may be considered to be a homomultimer, and one especially preferred molecule of this kind is a homodimer of an Fc binding region derived from an FcγRII type receptor. However, the present invention also contemplates that the molecule may be a multimer of an Fc binding region derived from an FcγR type receptor (e.g. an FcγRII type receptor) and an Fc binding region from another source (e.g. an Fc binding region from another Fc receptor type or a synthetic Fc binding polypeptide). A molecule of this kind may be considered to be a heteromultimer, and one especially preferred molecule of this kind is a heterodimer of an Fc binding region derived from an FcγRII type receptor and an Fc binding region derived from an FcγRIII type receptor.

The Fc binding regions may be linked through a peptide bond or via a short linker sequence (e.g. a single amino acid or a short peptide of, for example, 2 to 20 amino acids in length). Alternatively, the Fc binding regions may be linked through fused polypeptide domains that are capable of binding to one another (e.g. the Fc binding regions may each be fused to an Fc domain of an immunoglobulin, such that the two Fc domains dimerise to produce a dimeric protein comprising two Fc binding regions). Further, a combination of these linking means can be used. For example, using a polypeptide having two linked Fc binding regions fused to an Fc domain of an immunoglobulin, a protein can be produced which is a dimer of the polypeptide and, consequently, comprises four Fc binding regions (i.e. a dimeric protein that is tetrameric for the Fc binding region).

In a second aspect, the present invention provides a polynucleotide molecule comprising a nucleotide sequence encoding a soluble multimeric protein or polypeptide according to the first aspect.

The polynucleotide molecule may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

Thus, in a third aspect, the present invention provides a recombinant host cell containing a polynucleotide molecule comprising a nucleotide sequence encoding a soluble multimeric protein or polypeptide according to the first aspect.

In a fourth aspect, the present invention provides a method for producing a protein or polypeptide, the method comprising the steps of;
 (i) providing a recombinant host cell containing a polynucleotide molecule comprising a nucleotide sequence encoding a soluble multimeric protein or polypeptide according to the first aspect,
 (ii) culturing said host cell in a suitable culture medium and under conditions suitable for expression of said soluble multimeric protein or polypeptide, and
 (iii) isolating said soluble multimeric protein or polypeptide from the culture medium.

In a fifth aspect, the present invention provides a method of treating a subject for an inflammatory disease, said method comprising administering to said subject a soluble multimeric protein or polypeptide according to the first aspect optionally in combination with a pharmaceutically- or veterinary-acceptable carrier or excipient.

BRIEF DESCRIPTION OF THE FIGURES

FIG. 1 provides the nucleotide sequence (and translated amino acid sequence) for one embodiment of the present invention, namely a head to tail homodimer construct of two FcγRIIa extracellular regions each comprising both FcγRIIa ectodomains, namely ectodomains 1 and 2. The FcγRIIa ectodomains 1 and 2 consist of amino acids 1 to 174 of the FcγRIIa polypeptide sequence with amino acids 1 to 88 comprising domain 1 and amino acids 89 to 174 comprising domain 2 (Hibbs et al., 1988; *Homo sapiens* Fc fragment of IgG, low affinity IIa receptor (CD32) (FCGR2A), mRNA, ACCESSION NM_021642; and Powell et al., 1999). In the figure, amino acids 1 to 182 are derived from the extracellular region of FcγRIIa, of which amino acids 1 to 174 comprise the FcγRIIa ectodomains 1 and 2 and amino acids 175 to 182 comprise the membrane proximal stalk (which in FcγRIIa links the ectodomains 1 and 2 to the transmembrane sequence). The first of the FcγRIIa extracellular regions comprising the dimer therefore consists of amino acids 1 to 182 and the second of the FcγRIIa extracellular regions consists of amino acids 184 to 362 (corresponding to amino acids 3 to 182 of FcγRIIa). The underlined amino acid represents a non-FcγRIIa linker amino acid residue, while the bolded amino acids highlight a C-terminal His6 tag.

(6) the rsFcγRIIa dimer fused to HSA; (7) purified rsFcγRIIa monomer standard; and (8) purified rsFcγRIIa dimer standard.

Figure 15:
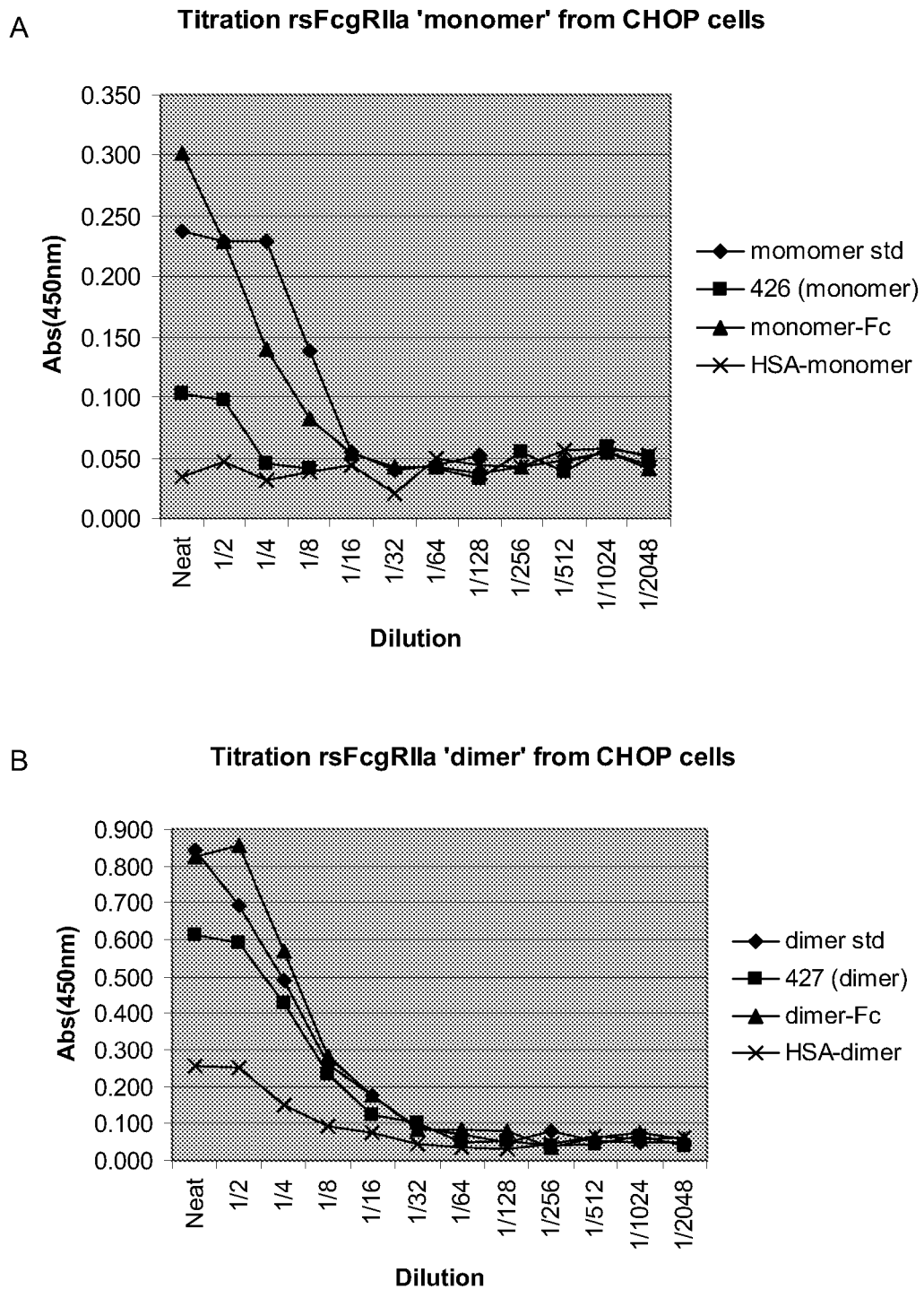

FIG. 15 provides the results of a HAGG-capture ELISA with rsFcγRIIa monomer and rsFcγRIIa dimer fusions. (a) FcγRIIa monomer standard (Powell et al., 1999) starting at 0.75 µg/ml (monomer std); protein from cells transfected with rsFcγRIIa monomer construct (transfection 426 (monomer)); protein from cells transfected with rsFcγRIIa monomer fusion to IgG-Fcγ1 (L234A, L235A) construct (monomer-Fc); and protein from cells transfected with rsFcγRIIa monomer fusion to HSA construct (HSA-monomer); (b) rsFcγRIIa dimer standard starting at 0.5 µg/ml (dimer std); supernatant from cells transfected with rsFcγRIIa dimer (transfection 427 (dimer)); supernatant from cells transfected with rsFcγRIIa dimer fusion to IgG-Fcγ1 (L234A, L235A) (dimer-Fc); and supernatant from cells transfected with rsFcγRIIa dimer fusion to HSA (HSA-dimer).

Figure 16:
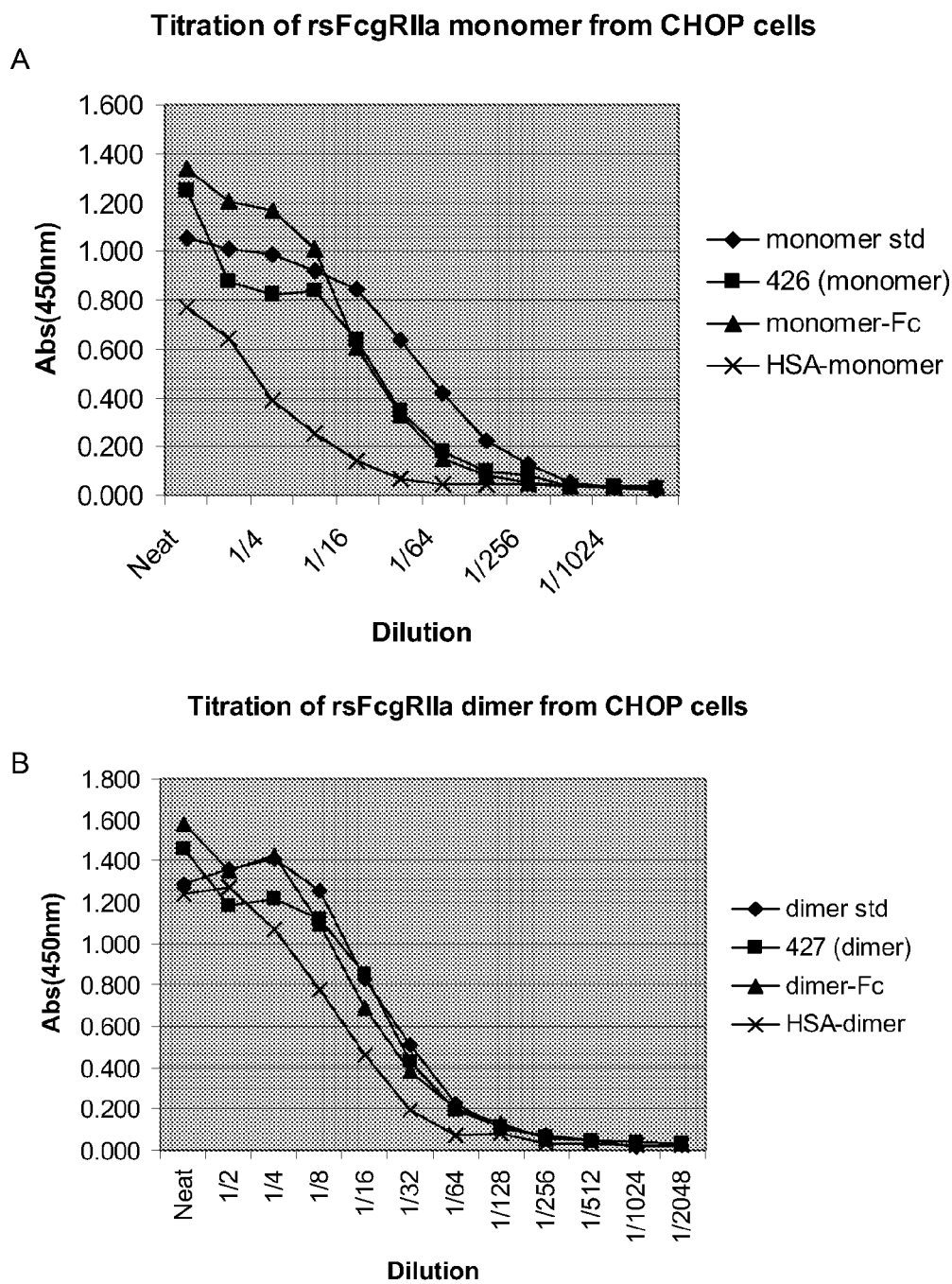

FIG. 16 provides results obtained from a CAPTURE-TAG ELISA on rsFcγRIIa monomer and rsFcγRIIa dimer fusion proteins to confirm the presence of epitopes that establish that the receptor is properly folded. (A) rsFcγRIIa monomer standard starting at 0.75 µg/ml (monomer std); supernatant from cells transfected with rsFcγRIIa monomer (transfection 426 (monomer)); supernatant from cells transfected with rsFcγRIIa monomer fusion to IgG-Fcγ1 (L234A, L235A) (monomer-Fc); and supernatant from cells transfected with rsFcγRIIa monomer fusion to HSA (HSA-monomer); (B) rsFcγRIIa dimer standard (prepared in-house) starting at 0.5 µg/ml); supernatant from cells transfected with FcγRIIa dimer (transfection 427 (dimer)); supernatant from cells transfected with rsFcγRIIa dimer fusion to IgG-Fcγ1 (L234A, L235A) (dimer-Fc); and supernatant from cells transfected with rsFcγRIIa dimer fusion to HSA (HSA-dimer).

Figure 17:
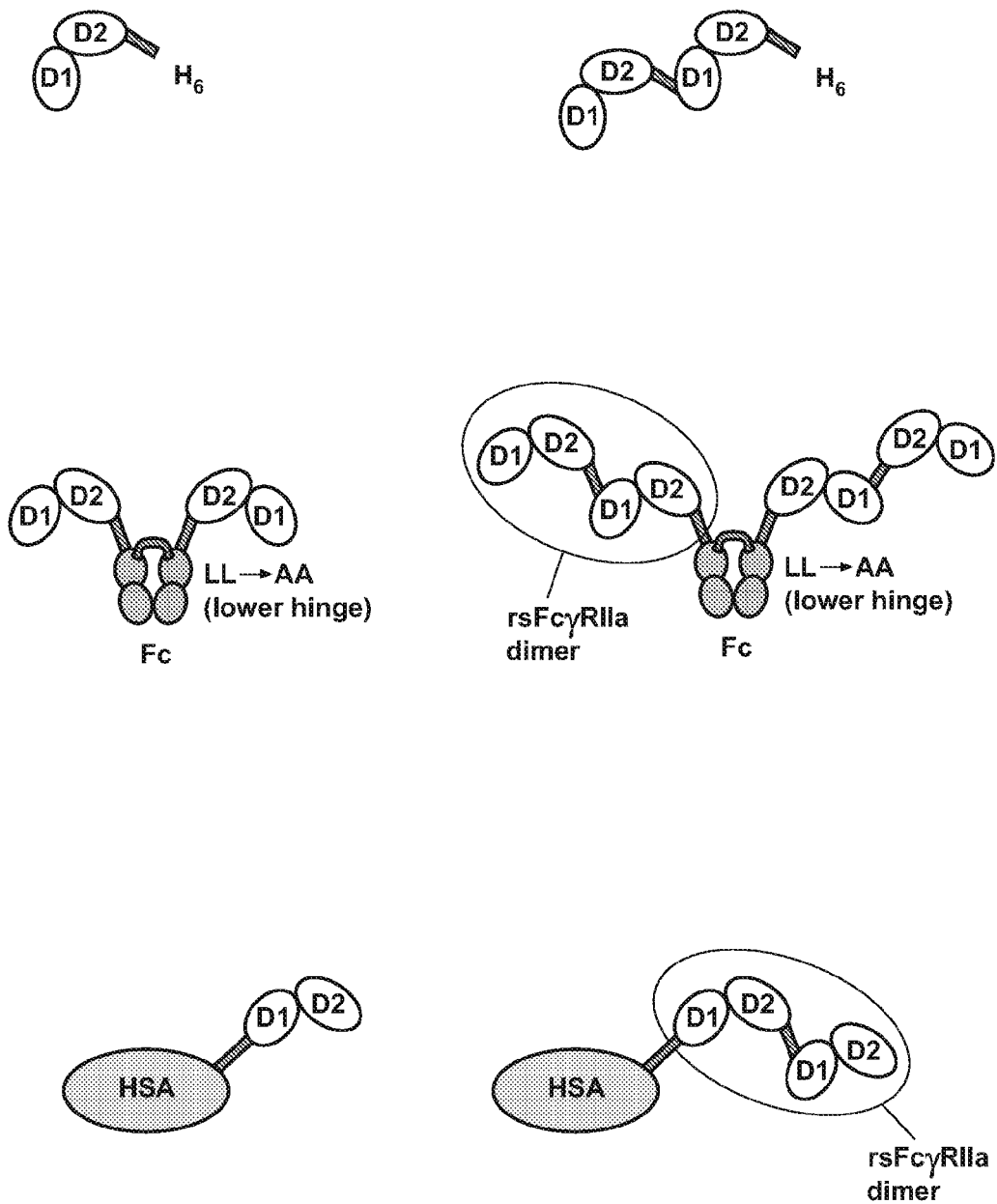
Figure 18:
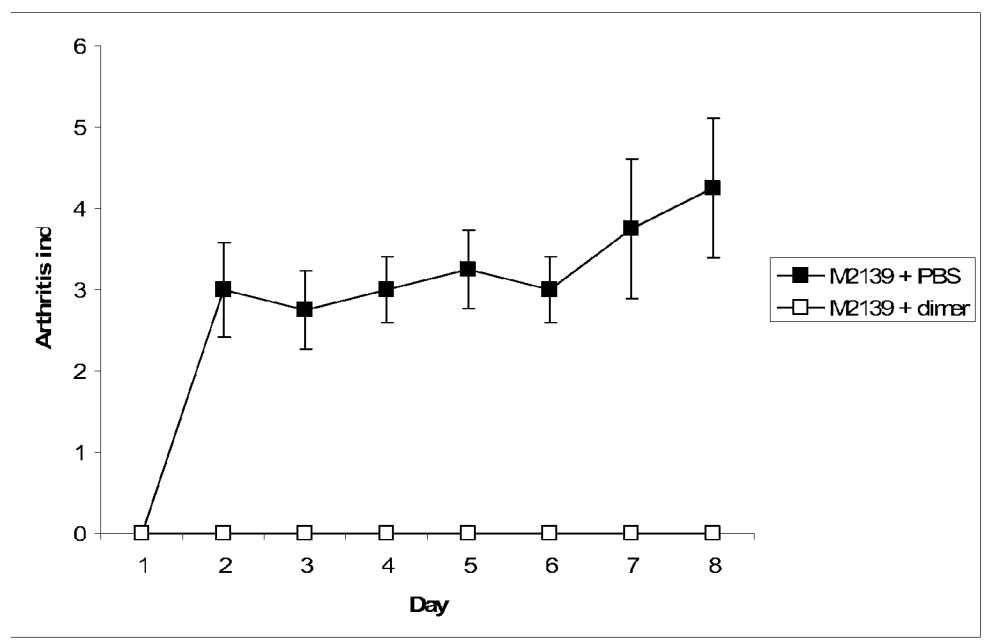
Figure 21:
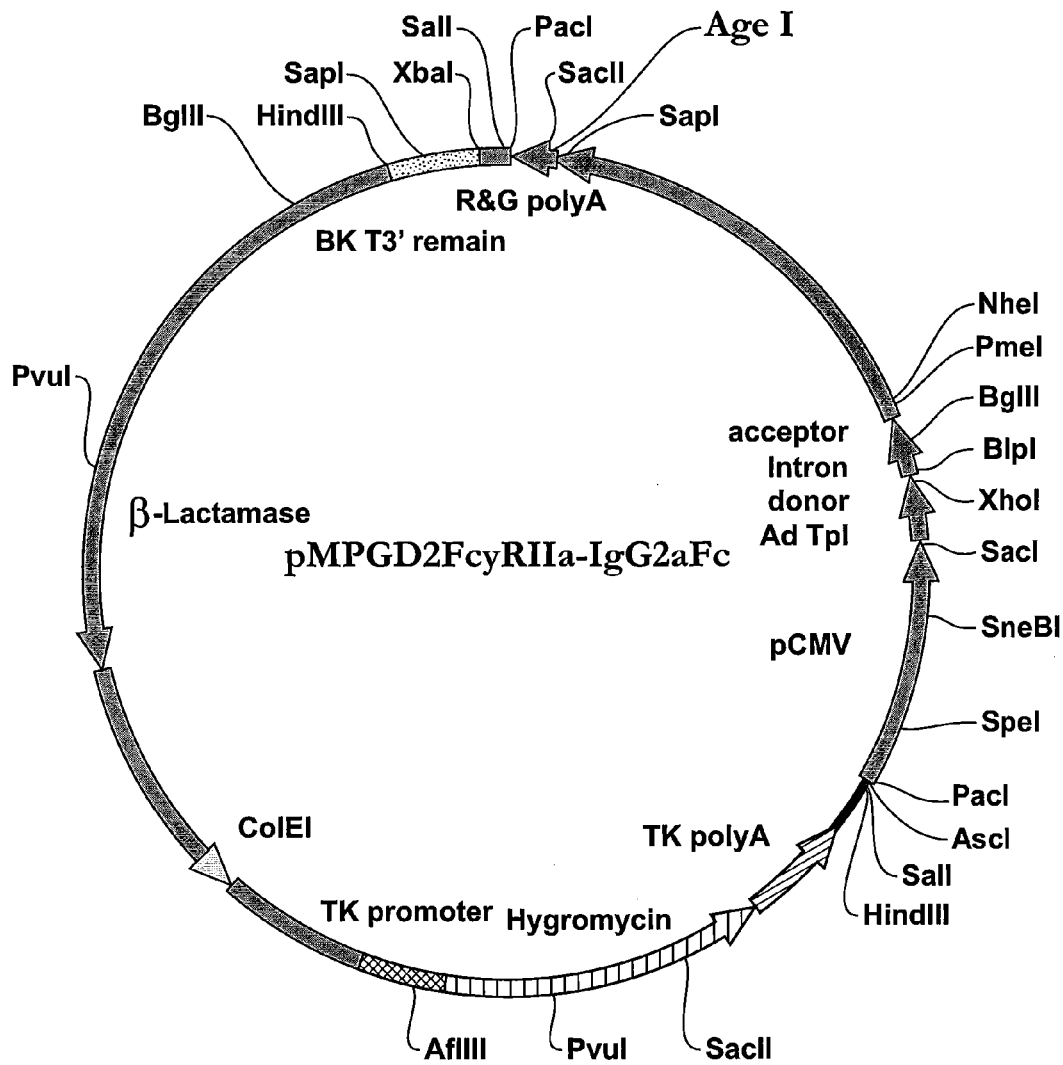
Figure 23:
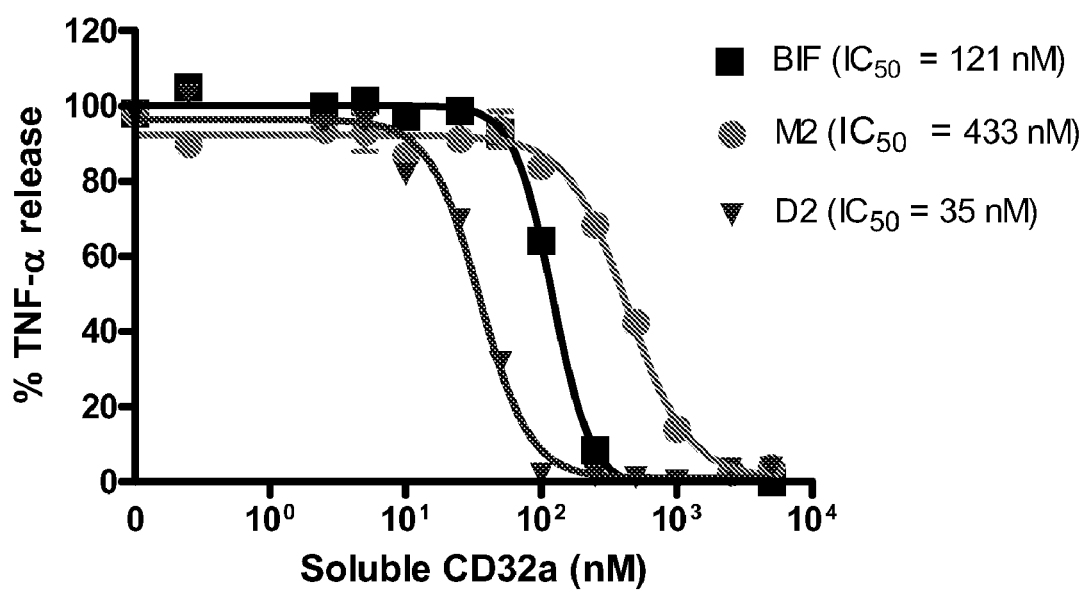
Figure 24:
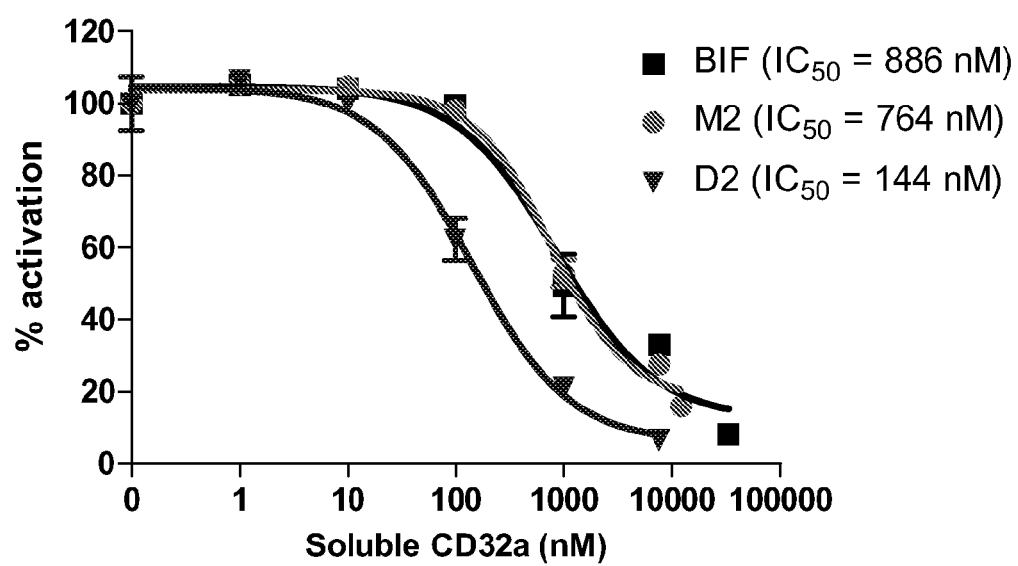
Figure 25:
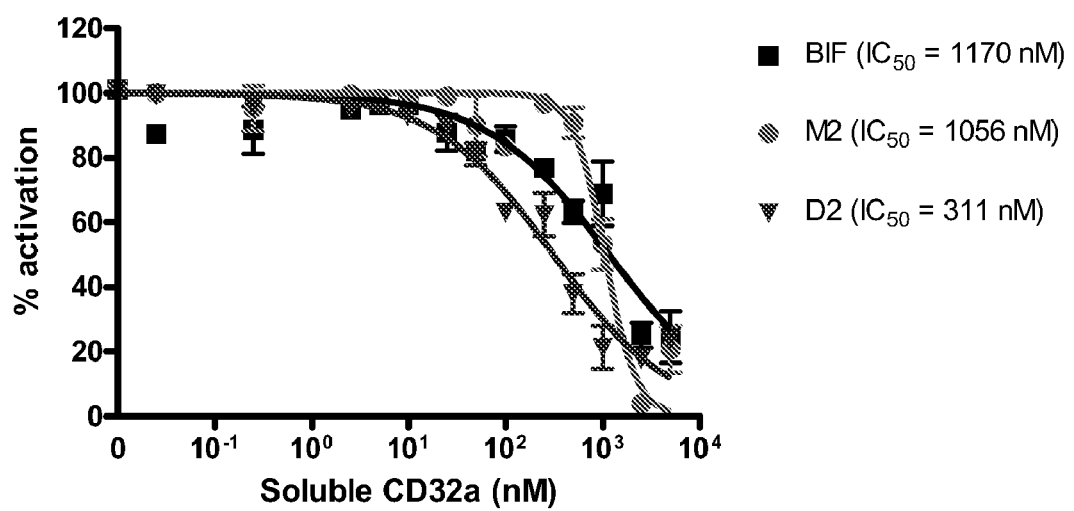

FIG. 17 provides a schematic diagram of (a) rsFcγRIIa monomer; (b) rsFcγRIIa dimer; (c) a dimer of a rsFcγRIIa monomer fusion to IgG-Fcγ1 (L234A, L235A), wherein the dimerisation is effected through the Fc domains of the rsFcγRIIa monomer fusion polypeptides, providing a molecule having two Fc binding regions (i.e. a protein that is dimeric for the Fc binding region or, otherwise, has a "valency of two"); (d) a dimer of rsFcγRIIa dimer fusion to IgG-Fcγ1 (L234A, L235A), wherein dimerisation is effected through the two Fc domains of the rsFcγRIIa dimer fusion polypeptides, providing a molecule having four Fc binding regions (i.e. a protein that is tetrameric for the Fc binding region or, otherwise, has a "valency of four"); (e) rsFcγRIIa monomer fusion to HSA; and (f) rsFcγRIIa dimer fusion to HSA. In the figure, D1 and D2 refers to, respectively, ectodomains 1 and 2, the solid bar shown adjacent to D2 represents a linker sequence, the dark loop at the top of the dimerised Fc domains in (c) and (d) represents disulphide linkages, and $H_6$ refers to a His tag);

FIG. 18 shows the effect of the rsFcγRIIa dimer (with no fusion partner) in a mouse model of arthritis. Mice treated with arthritogenic anti-collagen antibody in the absence (black square) and presence of the FcγRIIa dimer (white diamond);

FIG. 19 provides the amino acid sequence of another embodiment of the present invention, namely an rsFcγRIIa dimer fusion to an Fc domain derived from IgG2a (this fusion protein is hereinafter referred to as the D2 protein);

FIG. 20 provides the nucleotide sequence encoding the D2 protein of FIG. 19;

FIG. 21 illustrates the plasmid used to express the nucleotide sequence (encoding the D2 protein) of FIG. 20;

FIG. 22 shows an analysis of the purified D2 protein of FIG. 19 by SDS-PAGE (panel A) and by Western blot (panel B);

FIG. 23 shows the effect of the D2 protein (of FIG. 19) on TNF-α release in a MC/9 mast cell assay;

FIG. 24 shows the effect of the D2 protein (of FIG. 19) on human neutrophil activation; and FIG. 25 shows the effect of the D2 protein (of FIG. 19) on human platelet activation.

DETAILED DESCRIPTION OF THE INVENTION

The present invention provides a soluble multimeric protein or polypeptide able to inhibit interaction of leukocyte Fcγ receptors (FcγR) and immunoglobulin G (IgG) which comprises two or more Fc binding regions, one of which is essentially derived from an FcγR type receptor. Such a protein or polypeptide offers an increase in selectivity for immune complexes over that previously observed with soluble monomeric polypeptides such as rsFcγRII monomer, and thereby provides considerable promise as a "decoy" molecule for the treatment of IC-mediated inflammatory disease such as RA and SLE.

In a first aspect, the present invention therefore provides a soluble multimeric protein or polypeptide able to inhibit interaction of leukocyte Fcγ receptors (FcγR) and immunoglobulin G (IgG), said protein or polypeptide comprising two or more linked Fc binding regions, at least one of which is derived from an FcγR type receptor.

As used herein, the term "soluble" indicates that the protein or polypeptide is not bound to a cellular membrane, and is, accordingly, characterised by the absence or functional disruption of all or a substantial part of the transmembrane (i.e. lipophilic) domain, so that the soluble receptor is devoid of any membrane anchoring function. The cytoplasmic domains may also be absent.

As used herein, the term "Fc binding region" refers to any part or parts of an Fc receptor that is able to bind with an Fc domain of an immunoglobulin molecule (e.g. an Fc fragment produced by papain hydrolysis of an immunoglobulin molecule) including genetically modified versions thereof, as well as synthetic Fc binding polypeptides.

The at least one Fc binding region derived from an FcγR type receptor may be derived, for example, from an FcγR having low affinity for IgG, that is an affinity for IgG of less than $5 \times 10^7$ M$^{-1}$. Such low affinity receptors include FcγRII type receptors (e.g. FcγRIIa, FcγRIIb and FcγRIIc), FcγRIII type receptors (e.g. FcγRIIIa and FcγRIIIb), truncated forms of FcγRI type receptors (e.g. FcγRIa and FcγRIb) such as truncated polypeptides comprising the first and second of the three ectodomains of an FcγRI receptor (Hulett et al., 1991; Hulett et al., 1998), and genetically modified versions of FcγR which normally have high affinity for IgG but by virtue of the modifications (e.g. one or more amino acid substitution(s), deletion(s) and/or addition(s)) show a reduced affinity for IgG of less than $5 \times 10^7$ M$^{-1}$).

Preferably, the protein or polypeptide is a homomultimer of an Fc binding region derived from an FcγR receptor such as a low affinity FcγR. A suitable Fc binding region consists of all or an Fc binding part or parts of one or more ectodomains of an FcγR receptor. Persons skilled in the art will be able to readily identify Fc binding ectodomains of FcγR receptors since these domains belong to the IgG domain superfamily (Hulett et al., 1994, Hulett et al., 1995, Hulett et al., 1998, and Tamm et al., 1996) and are typically characterised by "a tryptophan sandwich" (e.g. residues W90 and W113 of FcγRIIa) and other residues (e.g. in FcγRIIa; residues of the ectodomain 1 and ectodomain 2 linker, and the BC (W113-V119), C'E (F132-P137) and FG (G159-Y160) loops of ectodomain 2 (Hulett et al., 1994)).

More preferably, the protein or polypeptide is a homomultimer of an Fc binding region of FcγRIIa. A suitable Fc binding region from FcγRIIa consists of all or an Fc binding part or parts of the ectodomains 1 and 2 of FcγRIIa. The FcγRIIa ectodomains 1 and 2 are found within amino acids 1 to 172 of the FcγRIIa amino acid sequence (Hibbs et al., 1988, and ACCESSION NM_021642). An example of an Fc binding part of the FcγRIIa ectodomains 1 and 2 is a fragment comprising amino acids 90 to 174 of the FcγRIIa amino acid sequence, which includes residues of the ectodomain 1 and ectodomain 2 linker and BC (W113-V119), C'E (F132-P137) and FG (G159-Y160) loops of ectodomain 2. X-ray crystallography studies has revealed that within this fragment, amino acids 113-116, 129, 131, 133, 134, 155, 156 and 158-160 make important contributions to the fragment surface that is able to bind to the Fc domain of IgG (International patent specification no WO 2005/075512).

The protein or polypeptide may also be a heteromultimer of an Fc binding region derived from an FcγRII type receptor and an Fc binding region from another source (e.g. an Fc binding region from another Fc receptor type such as another FcγR type or an Fc binding region from other immunoglobulin receptors such as receptors for IgA and IgE). One especially preferred molecule of this kind is a heterodimer of an Fc binding region derived from an FcγRII type receptor (particularly, FcγRIIa) and an Fc binding region derived from an FcγRIII type receptor.

Fc binding regions considered as having been "derived from" a particular Fc receptor include Fc binding regions having an amino acid sequence which is equivalent to that of an Fc receptor as well as Fc binding regions which include one or more amino acid modification(s) of the sequence of the Fc binding region as found in an Fc receptor. Such amino acid modification(s) may include amino acid substitution(s), deletion(s), addition(s) or a combination of any of those modifications, and may alter the biological activity of the Fc binding region relative to that of an Fc receptor (e.g. the amino acid modification(s) may enhance selectivity or affinity for immune complexes; such modifications at amino acids 133, 134, 158-161 are described in International patent specification no WO 96/08512). On the other hand, Fc binding regions derived from a particular Fc receptor may include one or more amino acid modification(s) which do not substantially alter the biological activity of the Fc binding region relative to that of an Fc receptor. Amino acid modification(s) of this kind will typically comprise conservative amino acid substitution(s). Exemplary conservative amino acid substitutions are provided in Table 1 below. Particular conservative amino acid substitutions envisaged are: G, A, V, I, L, M; D, E, N, Q; S, C, T; K, R, H: and P, Nα-alkylamino acids. In general, conservative amino acid substitutions will be selected on the basis that they do not have any substantial effect on (a) the structure of the polypeptide backbone of the Fc binding region at the site of the substitution, (b) the charge or hydrophobicity of the polypeptide at the site of the substitution, and/or (c) the bulk of the amino acid side chain at the site of the substitution. Where an Fc binding region including one or more conservative amino acid substitutions is prepared by synthesis, the Fc binding region may also include an amino acid or amino acids not encoded by the genetic code, such as γ-carboxyglutamic acid and hydroxyproline and D-amino acids.

TABLE 1

Exemplary conservative amino acid substitutions

| | Conservative Substitutions |
|---|---|
| Ala | Val*, Leu, Ile |
| Arg | Lys*, Gln, Asn |
| Asn | Gln*, His, Lys, Arg, Asp |
| Asp | Glu*, Asn |
| Cys | Ser |
| Gln | Asn*, His, Lys, |
| Glu | Asp*, γ-carboxyglutamic acid (Gla) |
| Gly | Pro |
| His | Asn, Gln, Lys, Arg* |
| Ile | Leu*, Val, Met, Ala, Phe, norleucine (Nle) |
| Leu | Nle, Ile*, Val, Met, Ala, Phe |
| Lys | Arg*, Gln, Asn, ornithine (Orn) |
| Met | Leu*, Ile, Phe, Nle |
| Phe | Leu*, Val, Ile, Ala |
| Pro | Gly*, hydroxyproline (Hyp), Ser, Thr |
| Ser | Thr |
| Thr | Ser |
| Trp | Tyr |
| Tyr | Trp, Phe*, Thr, Ser |
| Val | Ile, Leu*, Met, Phe, Ala, Nle |

*indicates preferred conservative substitutions

The Fc binding regions may be linked through a peptide bond or via a short linker sequence (e.g. a single amino acid or a short peptide of, for example, 2 to 20 amino acids in length). Alternatively, the Fc binding regions may be linked through fused polypeptide domains that are capable of binding to one another (e.g. Fc domains of immunoglobulins, avidin and biotin and fragments thereof capable of binding to one another, leucine zippers and other self-associating domains). Further, a combination of these linking means can be used. Moreover, it may in certain circumstances be preferable or desirable to link the Fc binding regions through other suitable linkage means (e.g. by chemical cross-linking).

Preferably, the protein or polypeptide of the present invention comprises a polypeptide wherein the Fc binding regions are linked in a "head to tail" arrangement. That is, the C-terminal ("tail") of a first Fc binding region will be linked to the N-terminal ("head") of a second Fc binding region. There will be at least two Fc binding regions, typically 2 to 4 Fc binding regions, linked in this manner, however the polypeptide may have up to 10 or more (e.g. 20) Fc binding regions linked in a head to tail arrangement. The Fc binding regions will typically be linked through a peptide bond or via a short linker sequence (e.g. a single amino acid or a short peptide of, for example, 2 to 20 amino acids in length or, more preferably, 2 to 15 amino acids in length, 2 to 10 amino acids in length, 2 to 8 amino acids in length, or, most preferably, 2 to 5 amino acids in length). Suitable short linker sequences may be short random sequences or may comprise short non-Fc binding region fragments of FcγR (e.g. short fragments of 20 or fewer amino acids from the proximal region of the membrane stalk of FcγR). The linker sequence may be a synthetic linker sequence such as, for example, GGGGSGGGS (SEQ ID NO: 4) which has a low susceptibility to proteolysis. Such a linker sequence may be provided in the form of 2 to 5 tandem "Gly4Ser" units. Linking the Fc binding regions through a peptide bond or a short linker sequence allows for the production of the polypeptide using recombinant expression systems.

Thus, in a first particularly preferred embodiment of a polypeptide according to the invention, the polypeptide comprises two or more Fc binding regions derived from FcγRIIa linked in a head to tail arrangement.

In a second particularly preferred embodiment of a polypeptide according to the invention, the polypeptide comprises two to four Fc binding regions derived from FcγRIIa linked in a head to tail arrangement.

In a third particularly preferred embodiment of a polypeptide according to the invention, the polypeptide comprises two Fc binding regions from FcγRIIa linked in a head to tail arrangement.

And in a fourth particularly preferred embodiment of a polypeptide according to the invention, the polypeptide comprises two FcγRIIa extracellular regions each comprising ectodomains 1 and 2, wherein said extracellular regions are linked in a head to tail arrangement through a linker comprising 1 to 20 amino acids.

The polypeptide of the present invention may further comprise a carrier protein or polypeptide (i.e. such that the polypeptide is a "fusion" of the carrier protein or polypeptide and said two or more linked Fc binding regions). The carrier protein may be any suitable carrier protein or polypeptide well known to persons skilled in the art, but preferably, is human serum albumin (HSA) or another carrier protein commonly used to improve bioavailability (i.e. through increasing the serum half life of the polypeptide when administered to a subject). Conveniently, the carrier protein can be fused to the polypeptide by expressing the polypeptide as a fusion protein with the said carrier protein in accordance with any of the methods well known to persons skilled in the art.

The polypeptide of the present invention may further comprise other useful linked molecules, for example, ethylene glycol (i.e. to produce a PEGylated polypeptide) to improve bioavailability, complement regulating molecules such a CD46, CD55 and CD59, cytokines (e.g. to enable delivery of cytokines to sites of inflammation) and cytokine receptors.

Further, as mentioned above, fused polypeptide domains that are capable of binding to one another, can be used as a means of linking two or more Fc binding regions to produce a protein or polypeptide according to the invention.

Thus, by using, for example, a polypeptide comprising a single Fc binding region fused to a polypeptide domain capable of binding to another polypeptide domain, which may be the same or different and which is fused to another polypeptide comprising a single Fc binding region, a protein can be produced which comprises two Fc binding regions (in other words, a dimeric protein comprising two linked Fc binding regions). Conveniently, this can be achieved through the use of an Fc domain of an immunoglobulin (e.g. an IgG such as $IgG_1$), since such an Fc domain is capable of dimerising (i.e. with another Fc domain). Preferably, the Fc domain is modified (e.g. by amino acid substitution(s) at residues critical for binding with Fc receptors) to prevent "self-binding" of the Fc domain to linked Fc binding regions, as well as to prevent binding to Fc receptors in vivo. In one especially preferred modified Fc domain for use in this manner, the Fc domain is derived from $IgG_1$ (Wines et al., 2000) and comprises amino acid modification at amino acid 234 and/or 235, namely $Leu^{234}$ and/or $Leu^{235}$. These leucine residues are within the lower hinge region of $IgG_1$ where the Fc receptor engages with the Fc domain. One or both of the leucine residues may be substituted or deleted to prevent Fc receptor engagement (i.e. binding); for example, one or both of $Leu^{234}$ and $Leu^{235}$ may be substituted with alanine (i.e. L234A and/or L235A) or another suitable amino acid(s) (Wines et al., 2000).

Similarly, by using a polypeptide comprising two or more Fc binding regions linked, for example, in a head to tail arrangement through a peptide bond, short linker sequence or other chemical cross-linking, that is fused to a polypeptide domain capable of binding to another polypeptide domain, which may be the same or different and which is fused to another polypeptide comprising two or more linked Fc binding regions, a protein can be produced which comprises at least four Fc binding region (in other words, a multimeric protein comprising four or more linked Fc binding regions).

Thus, in certain embodiments of the present invention, there is provided an Fc fusion protein comprising Fc-fused polypeptides, each polypeptide comprising an Fc component and at least two Fc binding regions, linked for example in a head-to-tail arrangement (i.e. in tandem) either by direct fusion or through a suitable linker. Preferably, the Fc component of the Fc fusion protein is capable of coupling the two polypeptides (i.e. through dimerisation) but lacks the ability to bind to the Fc binding regions provided in each polypeptide. More preferably, the Fc component shows a reduced affinity for binding endogenous Fc receptors other than neonatal Fc receptors (FcRn), including, for example, FcγRI, FcγRII and FcγRIII. The Fc component comprising the Fc fusion protein of these embodiments can be derived from human IgG4, which binds Fcγ receptors poorly, or other IgG isotypes that have been mutated to reduce FcγR binding. Such mutations have been extensively described by, for example, Clark and colleagues, who have designed and described a series of mutant IgG1, IgG2 and IgG4 Fc domains and their FcγR binding properties (Armour et al., 1999; Armour et al., 2002, the content of which is incorporated herein by reference in this application).

In certain embodiments of the invention, the Fc binding regions within the polypeptides are linked through a peptide linker constituting the membrane proximal stalk region of FcγRIIa, which is represented by the sequence PSMGSSSP (SEQ ID NO: 7). Equivalent linkers that adopt a similar secondary structure are also useful, including equivalents that incorporate conservative amino acid substitutions. Further, truncations and extensions of this amino acid sequence, having one or two fewer or additional amino acids, are also useful. Suitable linkers generally are those that permit the multimer to adopt a structure in which each Fc binding region in the multimer can participate in the binding of an Fc domain-bearing molecule. For example, the linker should permit the dimeric protein to bind a greater quantity of Fc domain-bearing molecules than are bound by the corresponding monomer. The selection of linkers suitable to this end can be made based on simple binding experiments, as exemplified herein.

In a second aspect, the present invention provides a polynucleotide molecule comprising a nucleotide sequence encoding a soluble multimeric protein or polypeptide according to the first aspect.

The polynucleotide molecule may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

For a soluble multimeric protein comprising a dimer of a polypeptide comprising at least one Fc binding region and a polypeptide domain (e.g. an Fc domain) capable of binding to another polypeptide domain, persons skilled in the art will appreciated that the encoding polynucleotide molecule will upon expression yield a single chain of the fusion polypeptide, which then will yield the desired multimeric protein (e.g. Fc domain-fused protein) as a product of host cell secretion.

Thus, in a third aspect, the present invention provides a recombinant host cell containing a polynucleotide molecule comprising a nucleotide sequence encoding a soluble multimeric protein or polypeptide according to the first aspect.

The recombinant host cell may be selected from bacterial cells such as *E. coli*, yeast cells such as *P. pastoris*, insect cells such as *Spodoptera* Sf9 cells, mammalian cells such as Chinese hamster ovary (CHO), monkey kidney (COS) cells and human embryonic kidney 293 (HEK 293) cells, and plant cells.

In a fourth aspect, the present invention provides a method for producing a protein or polypeptide, the method comprising the steps of;
  (i) providing a recombinant host cell containing a polynucleotide molecule comprising a nucleotide sequence encoding a soluble multimeric protein or polypeptide according to the first aspect,
  (ii) culturing said host cell in a suitable culture medium and under conditions suitable for expression of said soluble multimeric protein or polypeptide, and
  (iii) isolating said soluble multimeric protein or polypeptide from the culture, and, optionally, from the culture medium.

The protein or polypeptide may be isolated using any of the methods well known to persons skilled in the art. For example, the protein or polypeptide may be readily isolated using metal affinity chromatography techniques or using immobilised IgG or Heat-aggregated IgG (HAGG) chromatography techniques.

In a fifth aspect, the present invention provides a method of treating a subject for an inflammatory disease, said method comprising administering to said subject a soluble multimeric protein or polypeptide according to the first aspect optionally in combination with a pharmaceutically- or veterinary-acceptable carrier or excipient.

The method is suitable for treatment of inflammatory diseases such as IC-mediated inflammatory diseases including RA, ITP, SLE, glomerulonephritis and heparin-induced thrombocytopenia thrombosis syndrome (HITTS).

The subject will typically be a human, but the method of the fifth aspect may also be suitable for use with other animal subjects such as livestock (e.g. racing horses) and companion animals.

The term "pharmaceutically- or veterinary-acceptable carrier or excipient" is intended to refer to any pharmaceutically- or veterinary-acceptable solvent, suspending agent or vehicle for delivering the protein or polypeptide of the present invention to the subject.

The protein or polypeptide may be administered to the subject through any of the routes well known to persons skilled in the art, in particular intravenous (iv) administration, intradermal (id) administration and subcutaneous (sc) administration and oral and nasal administration. For subcutaneous administration, the administration may be achieved through injection or by a catheter inserted below the skin. Alternatively, subcutaneous administration may be achieved through sustained release implant compositions or injectable depot-forming compositions.

Typically, the protein or polypeptide will be administered at a dose in the range of 0.5 to 15 mg/kg body weight of the subject per day. Persons skilled in the art will, however, realise that the amount of an "effective dose" (i.e. a dose amount that will be effective in treating an inflammatory disease) will vary according to a number of factors including the age and general health of the subject and the severity of the inflammatory disease to be treated. It is well within the skill of persons skilled in the art to identify or optimise an appropriate effective dose amount for each particular subject.

In further aspects of the present invention, there is provided a composition comprising a soluble multimeric protein or polypeptide according to the first aspect optionally in combination with a pharmaceutically- or veterinary-acceptable carrier or excipient, and the use of a soluble multimeric protein or polypeptide in the manufacture of a medicament for the treatment of an inflammatory disease.

Further, the protein or polypeptide of the first aspect is also useful in applications other than the treatment of a subject for an inflammatory disease. That is, the protein or polypeptide can be used in diagnostic assays for detecting circulating immune complexes (IC) associated with the pathology of autoimmune diseases such as RA and SLE, wherein the protein or polypeptide can be used in a step of "capturing" IC (e.g. by binding the protein or polypeptide to a suitable substrate such as an ELISA plate) in place of the typical precipitation step (with polyethylene glycol) employed in such assays. After capturing IC from a sample (e.g. a serum or synovial fluid sample from a subject) to be assayed, the captured IC can be detected by using the protein or polypeptide in a form whereby it is linked to a molecule which might serve as a marker or reporter (e.g. radio-labelled molecules, chemiluminescent molecules, bioluminescent molecules, fluorescent molecules or enzymes such as horseradish peroxidase which can generate detectable signals). Alternatively, the captured IC could be detected or "probed" using antibodies specific for certain autoantigens (e.g. citrullene in RA, DNA in SLE, La/SS-B in Sjøgren's syndrome, and DNA topoisomerase I in scleroderma) to enable the determination of the level of specific autoantigens in circulating IC, which might allow for the development of assays for autoimmune diseases with improved diagnostic or prognostic results. Moreover, in a similar manner, IC captured by the protein or polypeptide of the present invention bound to a suitable substrate, could be detected or "probed" using antibodies specific for certain antigens of infectious pathogens (e.g. bacteria such as *Staphylococcus* and *Streptococcus*, parasites such as *P. falciparum* (malaria) and viruses such as hepatitis C virus (HCV), Epstein-Barr virus (EBV), human immunodeficiency virus (HIV) and arbovirus causative of Dengue fever), to provide information useful in identifying the causative pathogen of an infection, disease prognosis and/or the management of an infection.

Still further, the protein or polypeptide of the present invention is also useful in various bioassays wherein it can usefully inhibit the release of tumour necrosis factor (TNF) from cells including macrophages, dendritic cells (DC) and neutrophils. Moreover, when linked to a molecule which might serve as a marker or reporter such as those mentioned above, the protein or polypeptide can be used in in vivo imaging of sites of inflammation.

Yet further, the protein or polypeptide of the present invention is useful for the removal of circulating IC associated with IC-mediated inflammatory diseases, wherein the protein or polypeptide is bound to a suitable substrate such as an inert bead, fibre or other surface and exposed to a biological fluid (particularly blood) from a subject containing IC complexes such that IC are captured and subsequently removed from the biological fluid. The treated biological fluid, which is substantially depleted of IC, can then be returned to the subject from which it was obtained.

In order that the nature of the present invention may be more clearly understood, preferred forms thereof will now be described with reference to the following non-limiting examples.

EXAMPLES

Example 1

Production, Purification and Characterisation of FcR Multimer Polypeptides

Materials and Methods
Construction of FcγRIIa Multimer Expression Vectors

The Fc binding region comprising the ectodomains 1 and 2 of human FcγRIIa were amplified by using the thermostable polymerase Pwo (Roche), the clone Hu3.0 (Hibbs et al, 1988, ACCESSION NM_021642) as cDNA template and the primers oBW10 GTAGCTCCCCCAAAGGCTG (SEQ ID NO: 1) and oBWT1 CTACCCGGGTGAAGAGCTGC-CCATG (SEQ ID NO: 2). The half SnaBI (all DNA modifying enzymes were from New England Biolabs) and SmaI sites are underlined. The blunt PCR product was ligated using T4 DNA ligase into the vector pPIC9 (Invitrogen, Life Technologies) at the EcoRI site filled in with Klenow fragment of DNA polymerase I yielding the vector pBAR14. To produce the vector pBAR28 encoding the tandem ectodomains of FcγRIIa, pBAR14 was digested with SnaBI into which site the SnaBI/SmaI fragment of pBAR14 was ligated.

A baculovirus vector for expressing FcγRIIa multimerised ectodomains was constructed as follows: The fragment encoding the FcγRIIa leader sequence and ectodomains 1 and 2 were obtained from pVL-1392 (Powell et al, 1999, and Maxwell et al, 1999) by digest with EcoRI and XbaI, and then ligated into the EcoRI/XbaI sites of modified pBACPAK9 (Invitrogen Life Tech) in which the BamHI site in the multiple cloning site had first been eliminated by digest with BamHI, filling in using Klenow fragment of DNA polymerase and re-ligation. This construct, vector pBAR69, was digested with BamHI to which was ligated the BamHI fragment of pBAR28 yielding vectors pBAR71, pBAR72 and pBAR73 encoding rsFcγRIIa dimer, trimer and tetramer respectively. Insert sizes were defined by EcoRI/XbaI digest and the correct orientation of the multimerising BamHI fragment was screened by PvuII digest using standard protocols.

The mammalian expression vectors encoding FcγRIIa monomer and dimer were produced as follows: The FcγRIIa cDNA clone Hu3.0 (Hibbs et al, 1988, and DEFINITION: *Homo sapiens* Fc fragment of IgG, low affinity IIa, receptor (CD32)(FCGR2A), mRNA, ACCESSION NM_021642) was amplified using accuprime Pfx PCR (Invitrogen, Life Technologies) and cloned into the Gateway™ vector pDONR™221 (Invitrogen, Life Technologies) using the BP Clonase™ reaction according to the manufacturer's instructions (Invitrogen Life Tech) yielding pNB6. PCR using polymerase accuprime Pfx of pNB6 with the primers oBW11 and oBW302 TCTCATCACCACCATCACCACGTCTAGACC-CAGCTTTCTTGTACAAAG (SEQ ID NO: 3), digest with SmaI and ligation with T4 ligase yielded pBAR390 encoding the rsFcγRIIa with C-terminal hexahistidine tag. Digestion of pBAR390 with BamHI and ligation of the BamHI fragment of pBAR28 yielded vector pBAR397, encoding rsFcγRIIa dimer. Pvu II digest was then used to screen for the orientation of the dimerising BamHI fragment and sequencing with ABI BigDye3.1 (Applied Biosytems) confirmed the target sequence. The Gateway LR clonase reaction (Invitrogen, Life Technologies) was then used to transfer the FcγRIIa monomer (pBAR390) or dimer (pBAR397) into Gateway™ reading frame-A cassette (Invitrogen, Life Technologies) adapted expression vector pAPEX3P (Evans et al, 1995, and Christiansen et al, 1996) to give the expression vectors pBAR426 and pBAR427. Likewise, the Gateway LR clonase reaction was used to transfer the FcγRIIa monomer (pBAR390) or dimer (pBAR397) into Gateway™ reading frame-A cassette (Invitrogen, Life Technologies) adapted expression vector pIRESneo (Clontech). FIG. 1 shows the polynucleotide sequence (and translated amino acid sequence) for the "head to tail" dimer construct of FcγRIIa within pBAR397 used to construct the expression vector pBAR427. The two repeats are shown as amino acids 1 to 174 (i.e. the first Fc binding region) and 184 to 362 (i.e. the second Fc binding region) and are linked via a short (8 amino acid sequence; residues 175 to 182) fragment of the FcγRIIa membrane proximal stalk plus an additional valine residue (residue 183 shown underlined in FIG. 1). Amino acids −31 to −1 of the sequence shown in FIG. 1 represent the natural leader sequence of FcγRIIa.

Production of rsFcγRIIa Monomer and Dimer Polypeptides

Expression of recombinant soluble FcγRIIa (rsFcγRIIa) monomer and dimer polypeptides in HEK 293E cells was performed by transfection with 5 μg of plasmid DNA (pBAR426, pBAR427) in 10 cm² wells and Lipofectamine 2000 reagent (Invitrogen, Life Technologies) or Transit reagent (BioRad Laboratories) according to the manufacturer's instructions. After 48 hours, the transfected cells were then selected by incubation in 4 μg/ml puromycin. Puromycin selected cells were then grown in 1% FCS supplemented CD293 media (Invitrogen, Life Technologies) to stationary phase. The recombinant product was subsequently purified by chromatography over immobilised Nickel (Qiagen) or cobalt (Clontech) columns and further purified using Superdex 200 or Superdex G75 (Amersham/Pharmacia) size exclusion chromatography.

Comparison of Affinity Measurements of rsFcγRIIa Monomer and Dimer Polypeptides

Using a standard BIAcore assay protocol (Wines et al, 2001; Wines et al, 2003), affinity measurements for purified rsFcγRIIa monomer and dimer were conducted; the rsFcγRIIa monomer or dimer was injected at varying concentrations over immobilised human IgG monomer (Sandoglobulin, Novartis) or heat-aggregated IgG (HAGG, Wines et al, 1988; Wines et al, 2003) for 60 minutes, after which time the surface was regenerated (Wines et al, 2003). The immobilisation of the human IgG monomer on the biosensor surface causes it to be a multivalent array which mimics an immune complex.

Comparison of Inhibitory Activity of rsFcγRIIa Monomer and Dimer Polypeptides

Purified rsFcγRIIa monomer and dimer were incubated with increasing concentrations of a solution of human IgG monomer (Sandoglobulin) and dimer-IgG (Wright et al, 1985). The amount of free receptor polypeptide was then measured by injecting over immobilised human IgG monomer in accordance with a standard BIAcore assay protocol.

Inhibition of Immune-Complex Binding to Human Cells by rsFcγRIIa Monomer and Dimer Polypeptides Binding of small immune-complexes (represented by dimer-IgG) to human neutrophils (volunteers V1 and V5) was determined in the absence and presence of purified rsFcγRIIa monomer and dimer polypeptides by flow cytometry analysis (Current Protocols in Immunology, Wiley Interscience).

Inhibition of TNF Secretion from Immune-Complex Stimulated MDMs (Monocyte-Derived Macrophages) by rsFcγRIIa Monomer and Dimer Polypeptides In a first experiment, peripheral mononuclear cells were extracted from human blood (volunteer V5), positively sorted for CD14 expression using an automacs sorter (Miltenyi Biotec) and allowed to differentiate for 24 hours in the presence of M-CSF to MDMs (monocyte-derived macrophages) prior to stimulation with varying concentrations of small immune-complexes (represented by dimer-IgG), in the absence and presence of rsFcγRIIa dimer (in supernatant at 2.5 μg/ml). TNF secretion from the MDMs was then measured by human TNF ELISA according to manufacturers' protocol (BD Pharmingen). In a second experiment, MDMs were similarly produced ex vivo from human blood (this time from volunteer V1) and allowed to differentiate for 24 hours prior to stimulation with varying concentrations of small immune-complexes (i.e. dimer-IgG), in the absence and presence of rsFcγRIIa dimer (in supernatant at 2.5 µg/ml).

Inhibition of Immune Complex Activation of Platelets by rsFcγRIIa Dimer Polypeptides Washed platelets were prepared by low speed centrifugation of whole blood (That et al, 2003) and stimulated with heat-aggregated IgG (HAGG). Activation of platelets was measured by increased surface expression of P-selectin (CD62P) by flow cytometry (Lau et al, 2004).

Results

Expression of rsFcγRIIa Monomer and Multimer Polypeptides from Insect Cells

Figure 2:
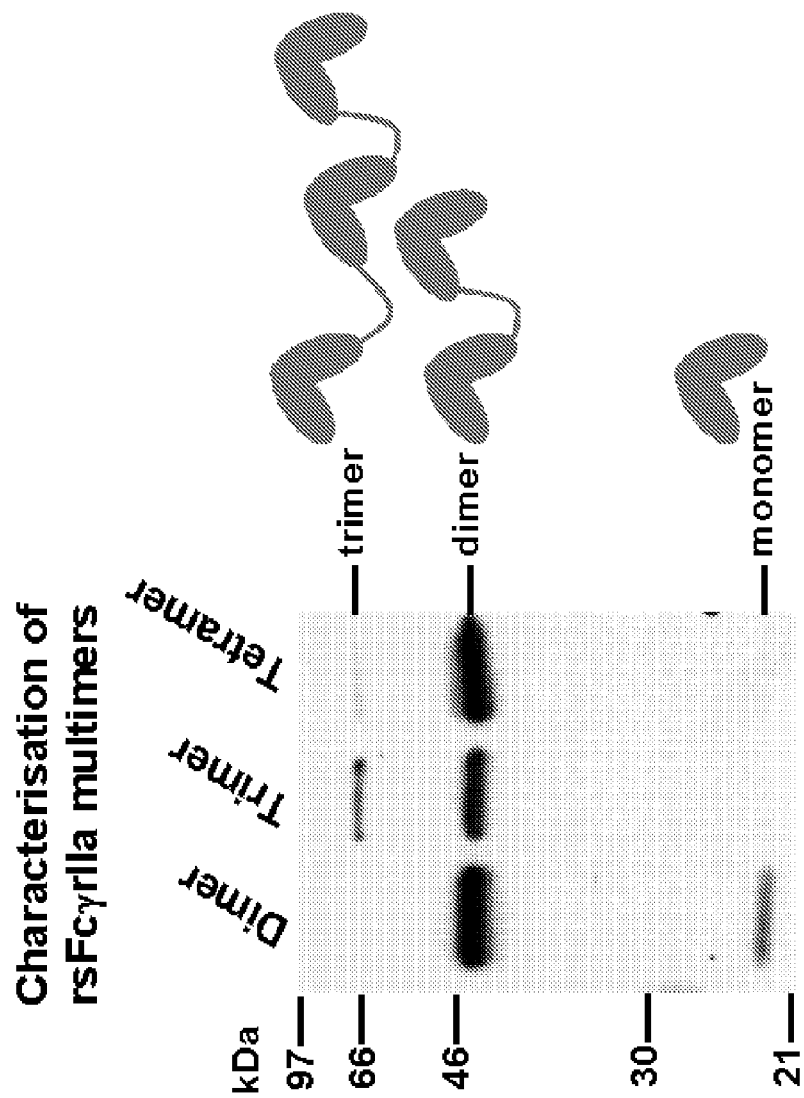
FIG. 2 shows a Western Blot analysis of recombinant soluble (rs) multimeric forms of FcγRIIa expressed from the nucleotide sequence shown in FIG. 1. The rsFcγRIIa dimer was substantially stable with only a small amount of rsFcγRIIa monomer breakdown product evident. On the other hand, the rsFcγRIIa trimer and tetramer forms were unstable, being substantially degraded to the rsFcγRIIa dimer form. This degradation may be avoided by the use of protease inhibitors during production or by otherwise modifying the sequence of the multimer forms so as to remove cleavage site(s).

Western blot analysis of infected cell supernatants demonstrated successful production of dimer and trimer forms of recombinant soluble FcγRIIa (FIG. 2). Although some trimer polypeptide was detected this was largely cleaved to the dimeric form and the tetramer was not detected being largely cleaved yielding a dimer form. Since the FcγRIIa dimer was intrinsically the most stable, this was further characterised and developed in a mammalian expression system (i.e. HEK293E cells).

However, since native FcγRIIa can be shed from leukocyte cell surfaces by proteolysis (Astier et al, 1994), one strategy for minimising proteolysis of the trimers, tetramers and larger multimers would be to eliminate or, more preferably, replace the membrane proximal stalk linker sequence linking the FcγRIIa extracellular regions. For example, the proteolytic susceptibility of membrane proximal stalk linker sequence could be reduced by one or more amino acid modifications (e.g. one or more amino acid substitution(s), deletion(s) and/or addition(s)) or by otherwise replacing that linker sequence with a synthetic linker sequence such as, for example, GGGGSGGGGS (SEQ ID NO: 4) which has a low susceptibility to proteolysis.

Another strategy for successfully producing trimers, tetramers and larger multimers, would be to link an expressed dimer polypeptide to one or more monomer or other dimer polypeptide(s) by chemical cross-linking. Multimers of FcγRIIa dimers may also be produced by expressing the dimer polypeptide as a fusion protein with an Fc domain (e.g. an IgG Fc domain) which is of itself dimeric and will thus dimerise any fusion partner.

Expression of rsFcγRIIa Monomer and Dimer Polypeptides from Mammalian Cells

Figures 3A, 3B:
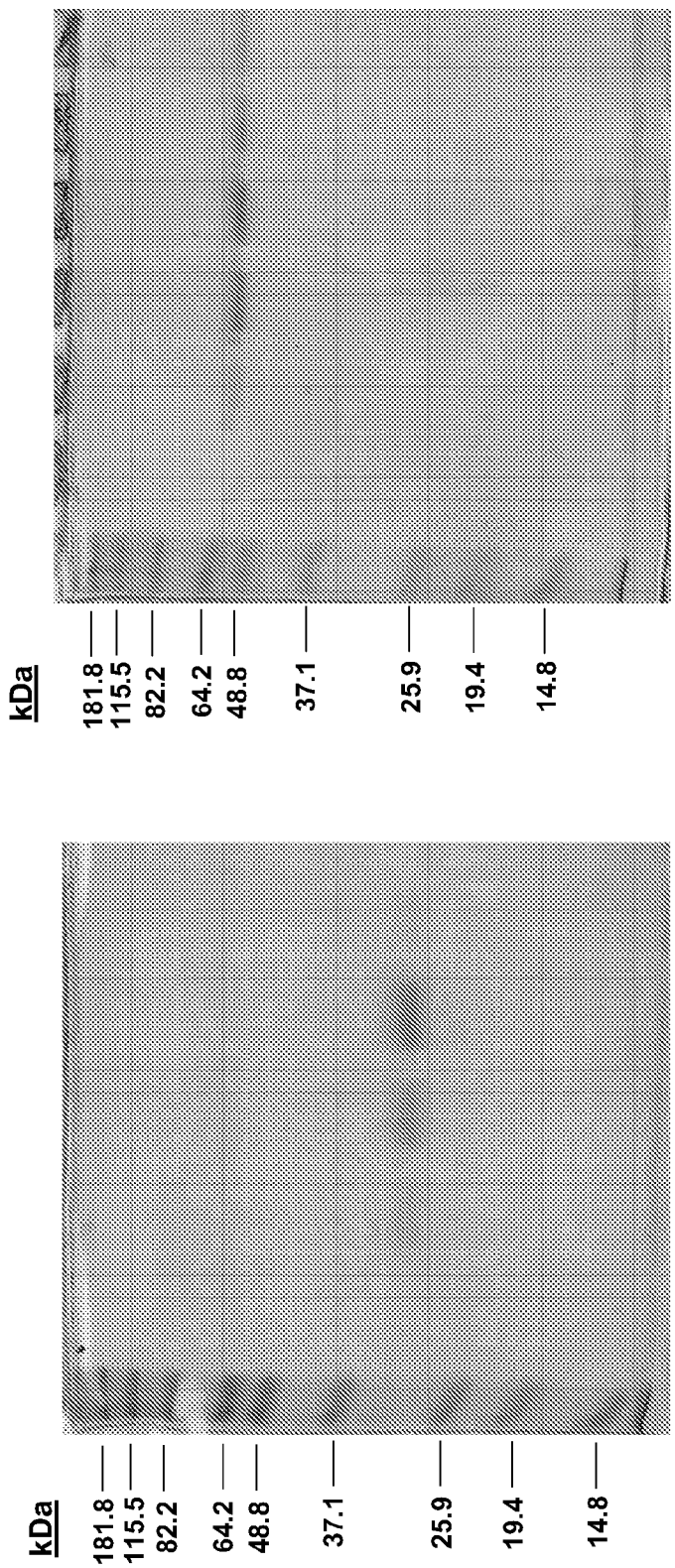
FIG. 3 shows a Coomassie-stained SDS-PAGE (12% acrylamide gel, under non-reducing conditions) of fractions collected from the purification of rsFcγRIIa monomer (expressed from mammalian cells) having the expected size of ~30 kDa (a), and rsFcγRIIa dimer having the expected size of ~50 kDa (b).

Protein yield for purified rsFcγRIIa monomer was 3 mg/l (construct pBAR 426) and for the rsFcγRIIa dimer, to ~0.5 mg/l (construct pBAR 427). FIG. 3 shows Coomassie-stained SDS-PAGE (12% acrylamide gel, under non-reducing conditions) of fractions collected from the purification of rsFcγRIIa monomer and dimer. The rsFcγRIIa monomer had the expected size of ~30 kDa (a), while the rsFcγRIIa dimer had the expected size of ~60 kDa (b).

Comparison of Affinity Measurements of rsFcγRIIa Monomer and Dimer Polypeptides

Figures 4A, 4B:
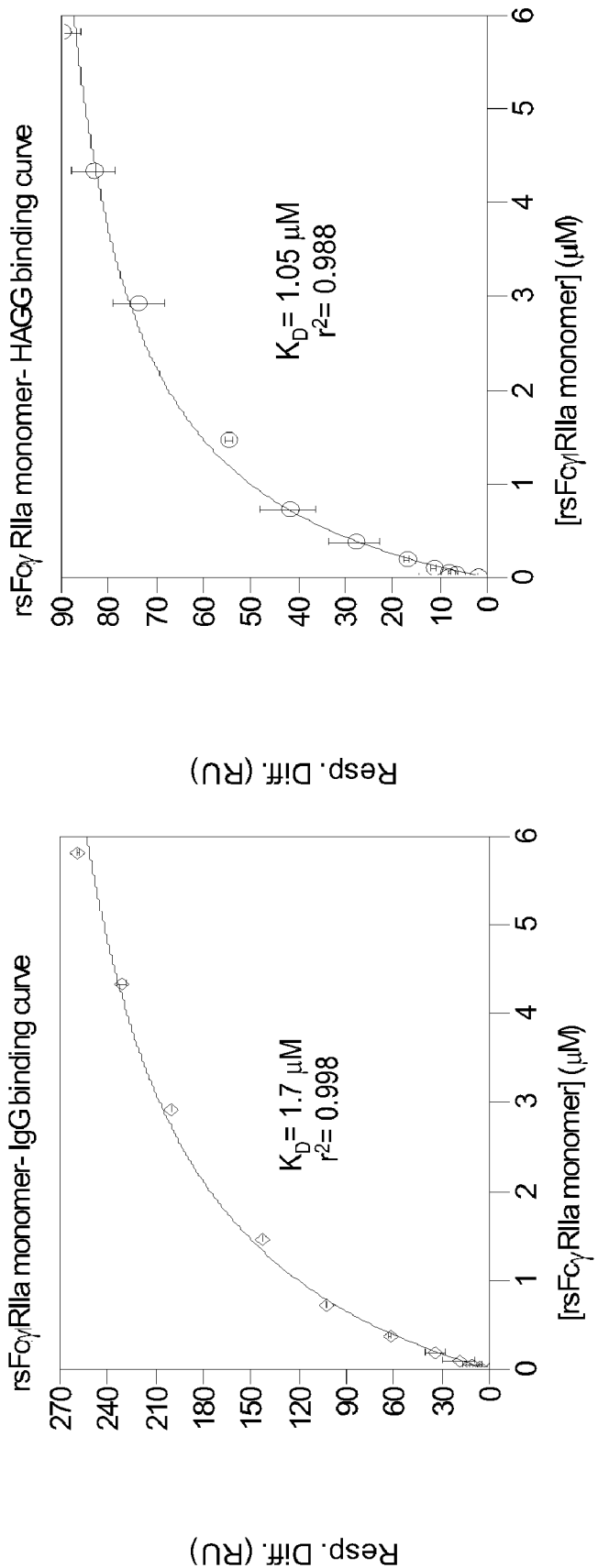
FIG. 4 graphically shows the equilibrium binding responses of rsFcγRIIa monomer to immobilised (a) IgG monomer (Sandoglobulin) and (b) the model immune complex, heat-aggregated IgG (HAGG).
Figures 5A, 5B:
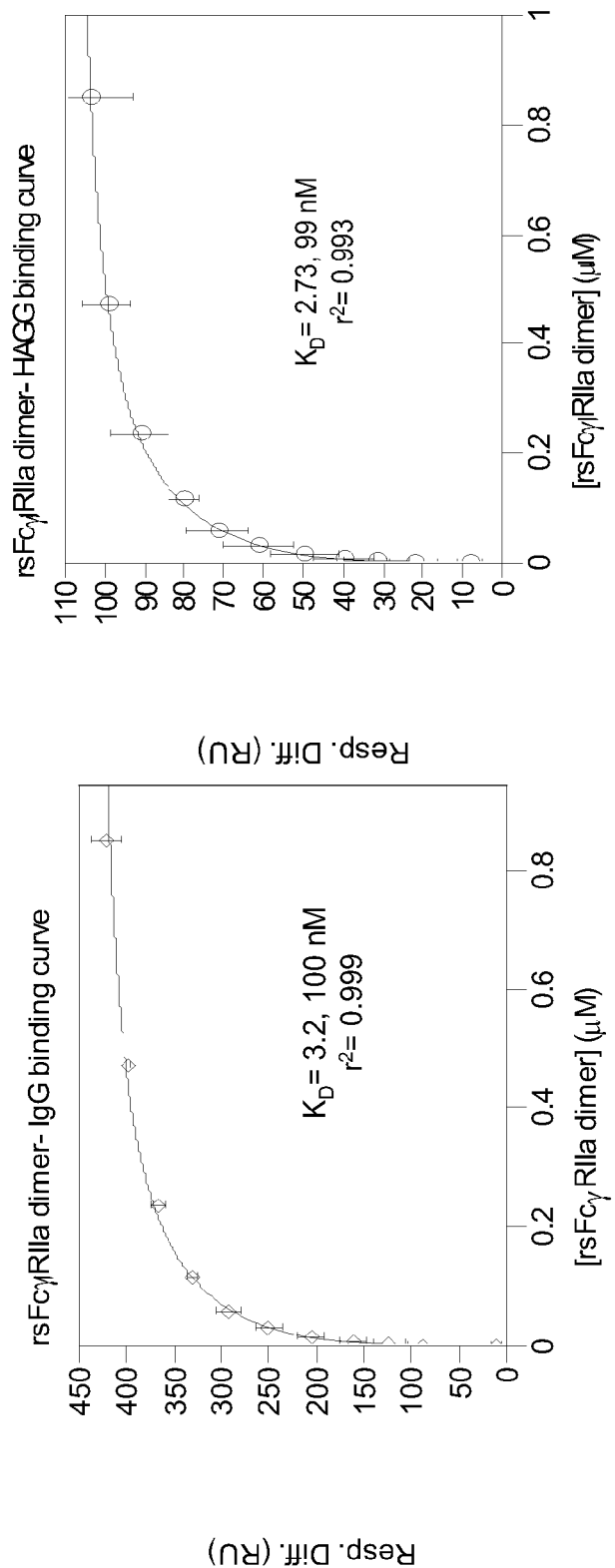
FIG. 5 graphically shows the equilibrium binding responses of rsFcγRIIa dimer to immobilised (a) IgG monomer (Sandoglobulin) and (b) the model immune complex, HAGG.

The results of the assays are shown in FIGS. 4 and 5. The assays indicated that rsFcγRIIa monomer has a single-binding site with affinity dissociation constant ($K_D$) of 1.7 µM for human IgG monomer and 1.05 µM for HAGG. In the case of the rsFcγRIIa dimer, the binding data best fitted a two-binding site model with affinity dissociation constants ($K_D$) of 3.2 nM ($K_{D1}$) and 100 nM ($K_{D2}$) for immobilised human IgG monomer and 2.73 nM ($K_{D1}$; approximated 300-fold lesser than the $K_D$ of monomeric rsFcγRIIa) and 99 nM ($K_{D2}$) for HAGG.

Comparison of Inhibitory Activity of rsFcγRIIa Monomer and Dimer Polypeptides

Figure 6B:
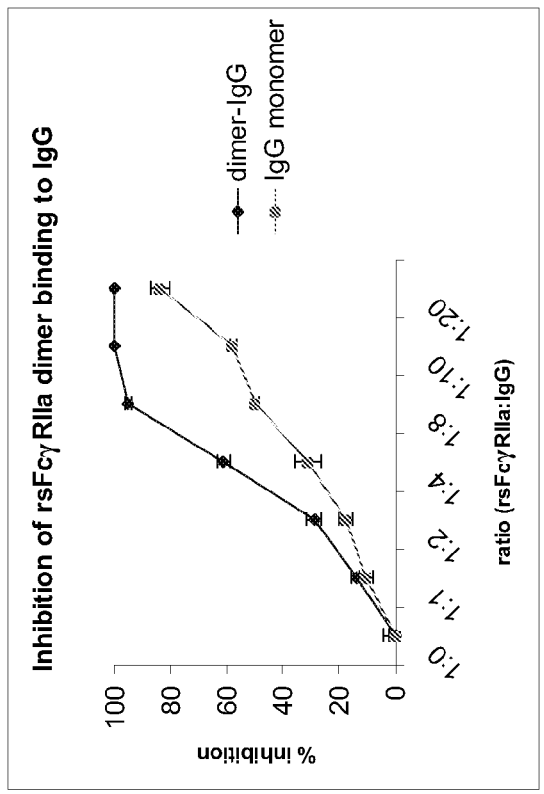
FIG. 6 provides a plot of rsFcγRIIa monomer (a) and rsFcγRIIa dimer expressed from the nucleotide sequence of FIG. 1 (b) binding to immobilised human IgG monomer (Sandoglobulin) following prior reaction in solution with human IgG monomer (Sandoglobulin) and dimer-IgG (Wright et al., 1980), as determined using a standard BIAcore assay protocol.
Figure 6A:
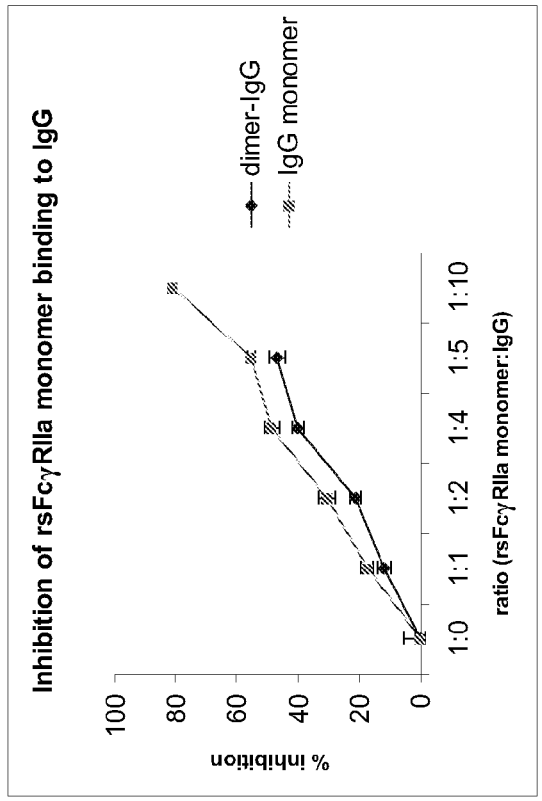

The experiments conducted to compare the inhibitory activity of the rsFcγRIIa monomer and dimer polypeptides showed that, in solution, rsFcγRIIa monomer (FIG. 6a) does not distinguish between human IgG monomer and small immune-complexes (i.e. represented by dimer-IgG). In contrast, rsFcγRIIa dimer (FIG. 6b) in solution, selectively binds to small immune-complexes (i.e. dimer-IgG) over human IgG monomer.

Figure 7A:
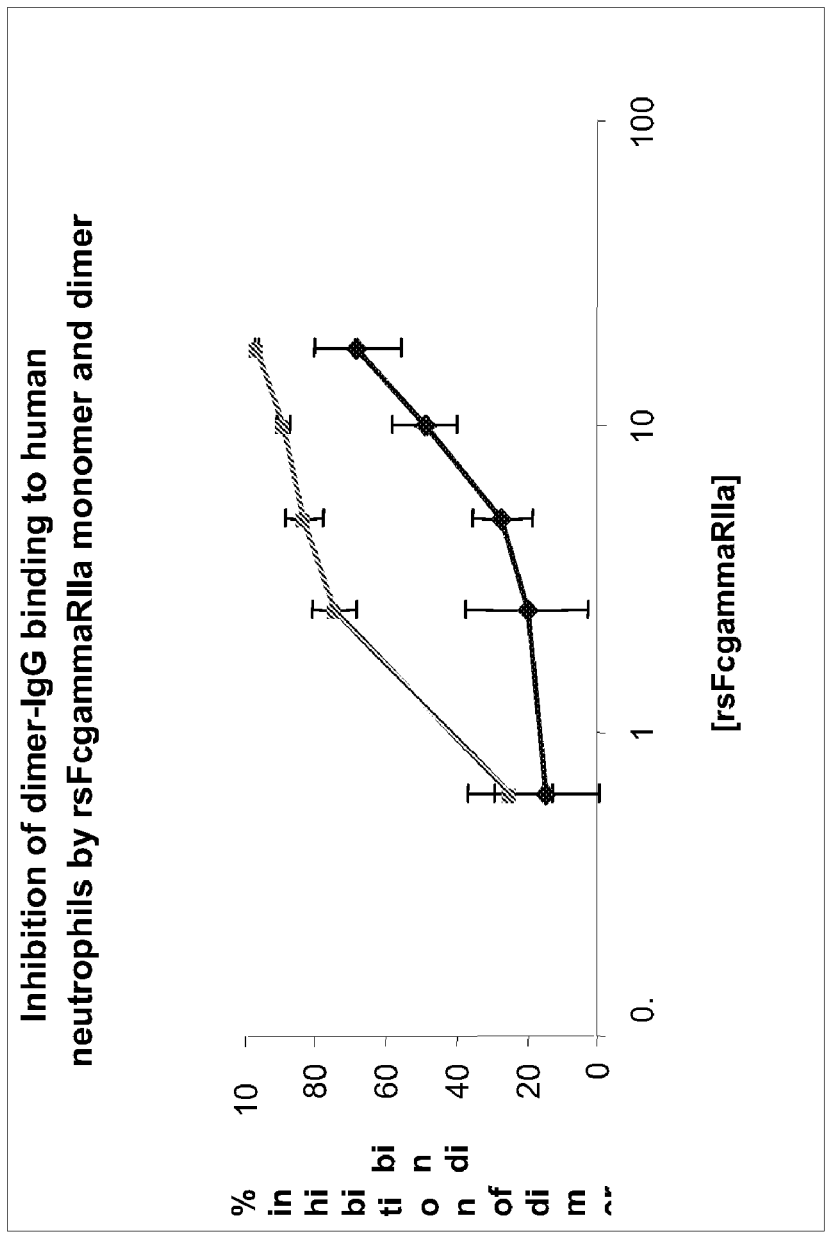
FIG. 7 provides plots of (a) the inhibition of dimer-IgG (Wright et al., 1980) binding to human neutrophils (volunteer V5) by purified rsFcγRIIa monomer and rsFcγRIIa dimer calculated as a percentage of the uninhibited dimer-IgG binding activity and (b) the inhibition of dimer-IgG binding to human neutrophils (volunteer V1) by purified rsFcγRIIa dimer (expressed from the nucleotide sequence of FIG. 1) calculated as a percentage of dimer-IgG binding dimer.
Figure 7B:
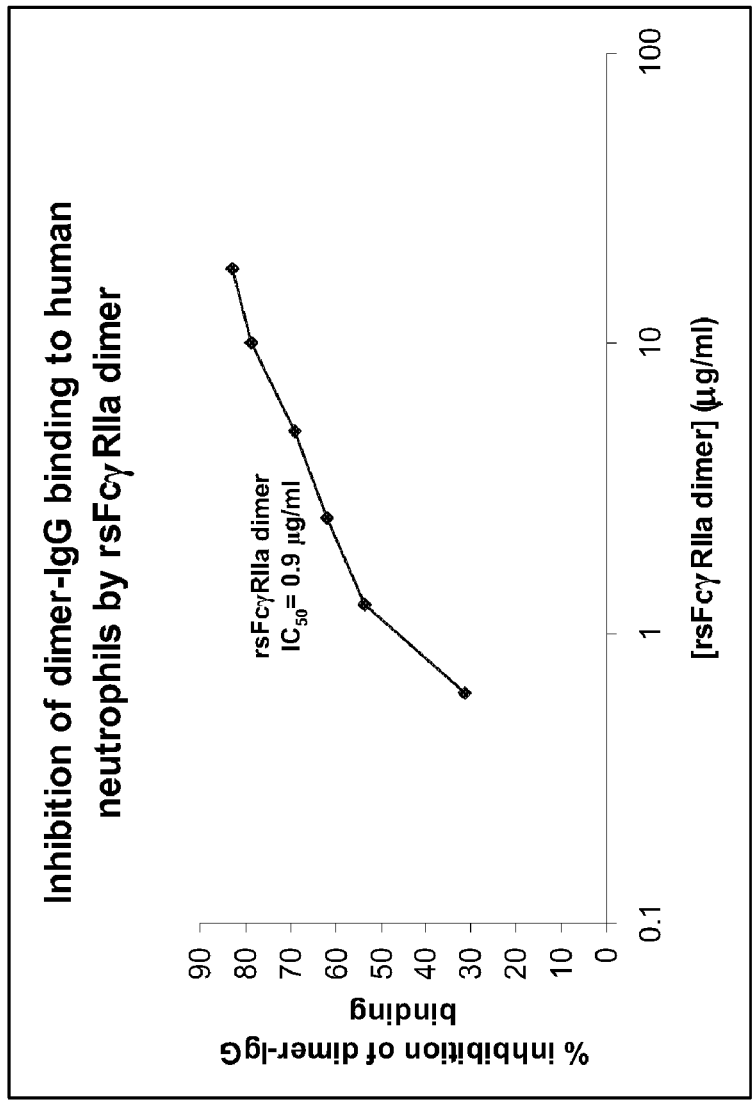

Inhibition of Immune-Complex Binding to Human Cells by rsFcγRIIa Monomer and Dimer Polypeptides The results of the inhibition assays are shown in FIGS. 7a and 7b, and these indicate that rsFcγRIIa dimer ($IC_{50}$=1.1 µg/ml) is ~10-fold more active than rsFcγRIIa monomer ($IC_{50}$=10.5 µg/ml) at inhibiting small immune-complexes (i.e. dimer-IgG) from binding to human neutrophils. Further, the results showed that the inhibition of small immune-complexes (dimer-IgG) from binding to human neutrophils by rsFcγRIIa dimer was reproducible with neutrophils from two different individuals, with an $IC_{50}$ of 0.9-1.1 µg/ml.

Figure 8B:
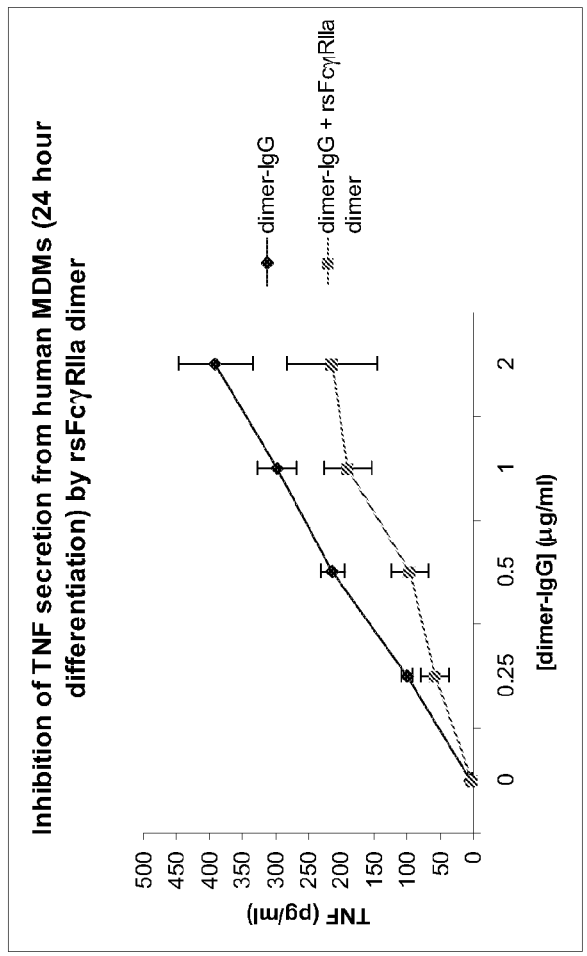
FIG. 8 provides at (a), a plot of immune-complex (dimer-IgG) stimulated TNF secretion from 24 hour differentiated human MDMs (volunteer V5) in the absence and presence of rsFcγRIIa dimer (in supernatant at 2.5 µg/ml); while at (b), provides a plot of immune-complex (dimer-IgG) stimulated TNF secretion from 24 hour differentiated human MDMs (volunteer V1), in the absence and presence of rsFcγRIIa dimer (2.5 µg/ml).
Figure 8A:
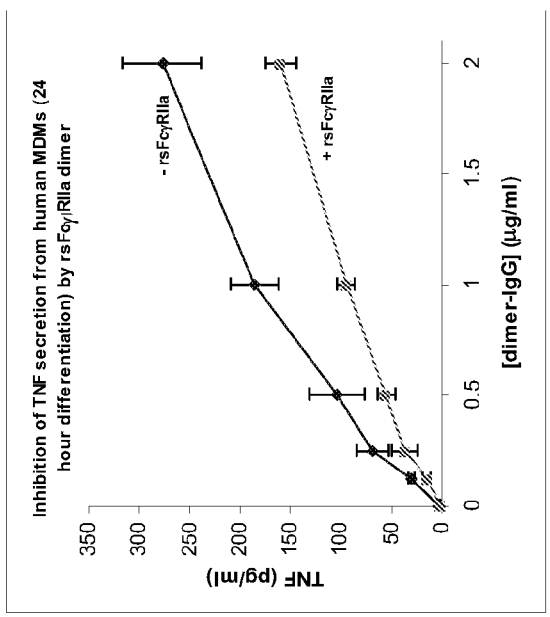

Inhibition of TNF Secretion from Immune-Complex Stimulated MDMs (Monocyte-Derived Macrophages) by rsFcγRIIa Monomer and Dimer Polypeptides The results are shown in FIGS. 8a and 8b. The rsFcγRIIa dimer appeared to inhibit immune-complex (i.e. dimer-IgG) stimulated TNF secretion from 24 hour differentiated human MDMs.

Figure 9:
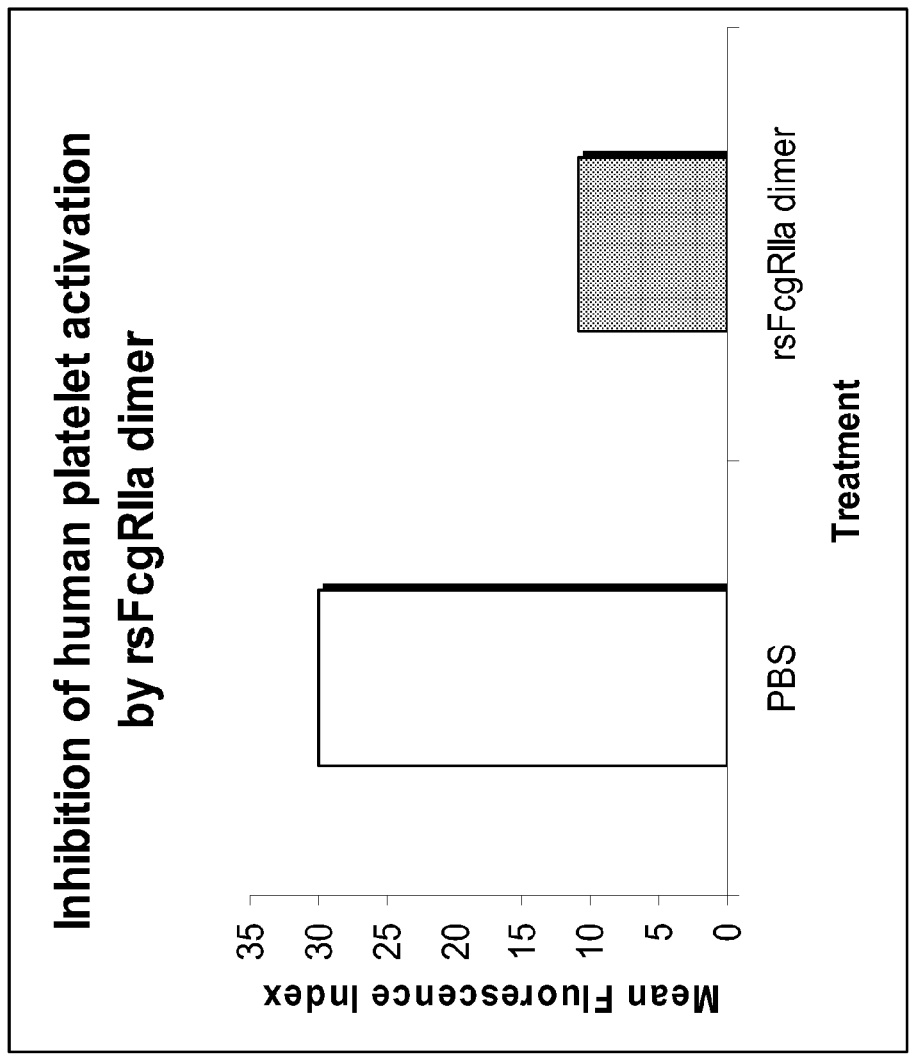
FIG. 9 provides a plot of immune-complex (HAGG) stimulated activation of human platelets, as measured by the mean fluorescence intensity (MFI) of P-selectin expression in the absence and presence of rsFcγRIIa dimer (30 µg/ml).

Inhibition of Immune Complex Activation of Platelets by rsFcγRIIa Dimer Polypeptides Washed human platelets were incubated with HAGG (10 µg/ml) in the presence and absence of rsFcγRIIa dimer at 30 µg/ml for 30 minutes. As shown in FIG. 9, it was found that the activation of platelets was inhibited in the presence of the rsFcγRIIa dimer as evidenced by the lesser expression of P-selectin (CD62P).

Discussion

Recombinant soluble FcγRIIa in the monomeric (rsFcγRIIa monomer) and dimeric (rsFcγRIIa dimer) form was successfully expressed in HEK 293E cells. BIAcore equilibrium binding assays demonstrated that the rsFcγRIIa dimer has an ~300 fold greater avidity for immobilised IgG (Sandoglobulin) than the monomeric receptor (i.e. the rsFcγRIIa monomer has a $K_D$~1 µM while the rsFcγRIIa dimer has a $K_D$~3 nM in the interaction with the immobilised IgG). Competition experiments using BIAcore also demonstrated that the rsFcγRIIa dimer selectively binds small immune complexes, and selective inhibitory activity was confirmed in cell based assays using neutrophils from two donors. The rsFcγRIIa dimer also proved to be about 10 times more potent an inhibitor of small IgG immune complex binding than the rsFcγRIIa monomer, and in a standard platelet assay, the rsFcγRIIa dimer was observed to completely inhibit immune complex activation of platelets (i.e. rsFcγRIIa dimer is a potent inhibitor of cell activation). It is therefore considered that rsFcγRIIa dimer and other soluble multimeric proteins and polypeptides according to the invention show considerable promise for the treatment of IC-mediated inflammatory disease such as RA and SLE.

Example 2

Production, Purification and Characterisation of RsfcγRIIa Dimer Polypeptide

Materials and Methods

Production of rsFcγRIIa Dimer Polypeptides

The FcγRIIa dimer construct described in Example 1 was cloned into a mammalian expression vector under the control of a modified CMV promoter. Stable CHO—S transfectants were then established as follows: CHO—S cells at 90% confluency were harvested, washed three times, and $2\times10^7$ cells in 15 ml medium were dispensed into 10 cm petri dishes. Linearised DNA-lipofectamine 2000 complexes (1:2.5 ratio) were then incubated for 5 minutes at room temperature and added dropwise to the cells. Subsequently, cells were incubated at 37° C. for 48 hours, and then plated out in limiting dilution in 96-well plates in CD-CHO medium supplemented with 600 µg/ml hygromycin B, 8 mM L-glutamine, 1×HT supplement and 50 µg/ml dextran sulfate. Cells were screened by standard ELISA to detect soluble FcγRIIa protein, and the highest expressing lines were subcloned again by limiting dilution. One clone (#6) secreted FcγRIIa dimer at approximately 40 mg/L and was cultured in shaker flasks at 30° C. for optimal protein expression.

Supernatant containing rsFcγRIIa dimer was concentrated by tangential flow filtration and exchanged into 20 mM sodium phosphate pH 7.4 buffer. The sample was then diluted four-fold in 20 mM sodium phosphate and 0.5 M sodium chloride and purified over a HisTrap FF 2×5 ml column (GE Healthcare), eluting in 20 mM sodium phosphate, 0.5 M sodium chloride pH 7.4 and 100 mM imidazole. The eluted material was dialysed and purified by ion exchange chromatography, using a 25 ml Q FF column (GE Healthcare) and eluting in 150 mM sodium chloride. The purified material was then dialysed into phosphate buffered saline.

Blocking of HAGG Binding to FcγRIIb with rsFcγRIIa Dimer Polypeptides

The ability of purified rsFcγRIIa dimer to block immune complex binding to cell surface FcγRIIb was assessed by a flow cytometric assay. Heat-aggregated IgG (HAGG) was incubated with various concentrations of rsFcγRIIa dimer or rsFcγRIIa monomer (R&D Systems, Cat #1330-CD/CF) for 1 hour at 4° C. These mixtures were then added to 96-well plates containing $10^5$ IIA1.6 cells transfected with human FcγRIIb (IIA1.6 is a mouse B lymphoma line that lacks endogenous FcγR expression). The plates were incubated for 1 hour at 4° C., washed and then stained with an anti-hIgG-FITC conjugate to detect bound HAGG. After washing, the cells were analysed on a FACS Scan flow cytometer using standard protocols.

Blocking of HAGG-Induced Platelet Activation with rsFcγRIIa Dimer Polypeptides

Exposure of platelets to HAGG results in activation via FcγRIIa, leading to upregulation of P-selectin (CD62P). The ability of rsFcγRIIa dimer or rsFcγRIIa monomer to block this activation was assessed by a flow cytometric assay. Heat-aggregated IgG (HAGG) was incubated with various concentrations of rsFcγRIIa dimer or rsFcγRIIa monomer (R&D Systems, Cat #1330-CD/CF) for 1 hour at 4° C. The mixture was then added to 96-well plates containing $3\times10^7$ human platelets, which had been previously washed and resuspended in Tyrodes/Hepes buffer supplemented with 1 mM EDTA. After a 30 minute incubation at room temperature, the cells were washed, fixed, and stained for CD62P and GPIIb (CD41) expression by standard methods and analysed on a FACS Scan flow cytometer.

rsFcγRIIa Dimer Polypeptides Block Immune Complex-Induced MC/9 Activation

MC/9 is an FcγR-positive murine mast cell line that becomes activated and releases TNF-α after exposure to immune complexes. The ability of rsFcγRIIa dimer or rsFcγRIIa monomer to block this activation was assessed using immune complexes consisting of ovalbumin and anti-ovalbumin antibody (OVA ICs) as a stimulus. OVA ICs (10 µg) were incubated with various concentrations of rsFcγRIIa dimer or rsFcγRIIa monomer (R&D Systems, Cat #1330-CD/CF) for 1 hour at room temperature. The mixture was then added to 96-well plates containing $2\times10^5$ MC/9 cells, and incubated overnight at 37° C. Supernatant was collected and the amount of TNF-α measured using a commercial ELISA kit (BD Biosciences).

rsFcγRIIa Dimer Inhibits Induced Arthritis in Human FcγRIIa Transgenic Mouse Model The activity of the rsFcγRIIa dimer was assessed in an arthritis model using the transgenic human FcγRIIa mice described in published PCT application WO03/104459, incorporated herein by reference. These mice express a transgene that encodes human FcγRIIa.

Clinically apparent arthritic disease (determined using the standard arthritis index) is elicited in these mice at least by Day 4 following administration of a single 2 mg dose of monoclonal antibody M2139 in PBS, which is an IgG2a that binds specifically to the J1 epitope of collagen II, amino acids 551-564. The monoclonal antibody is produced by hybridomas proven to be arthritogenic (Amirahmadi et al., *Arthritis and Rheumatism*, June 2005; Nandakumar et al., *Arthritis Research and Therapy*, May 2004).

The mice were treated using the soluble FcγRIIa dimer shown in FIG. 1, as follows: Four FcγRIIa Tg mice were injected with 0.5 mg soluble FcγRIIa dimer, and a control group of four mice were given PBS, i.p. Two hours later, both groups were injected with 2 mgs of M2139 (ip) and a bolus dose of 1 mg of dimer or PBS. Dimer (0.5 mg/dose) was given again at both 24 and 48 hours following injection of M2139. Arthritis was scored as usual, with a maximum score possible of 12. The sum of four paws each scored 0-3 (0=normal; 1=one affected joint, erythema, minor swelling; 2=Two or more affected joints, ankle/wrist swelling; 3=all joints affected, loss of mobility/ankylosis, profound erythema and oedema).

Results

Production of rsFcγRIIa Dimer Polypeptides

Figure 10:
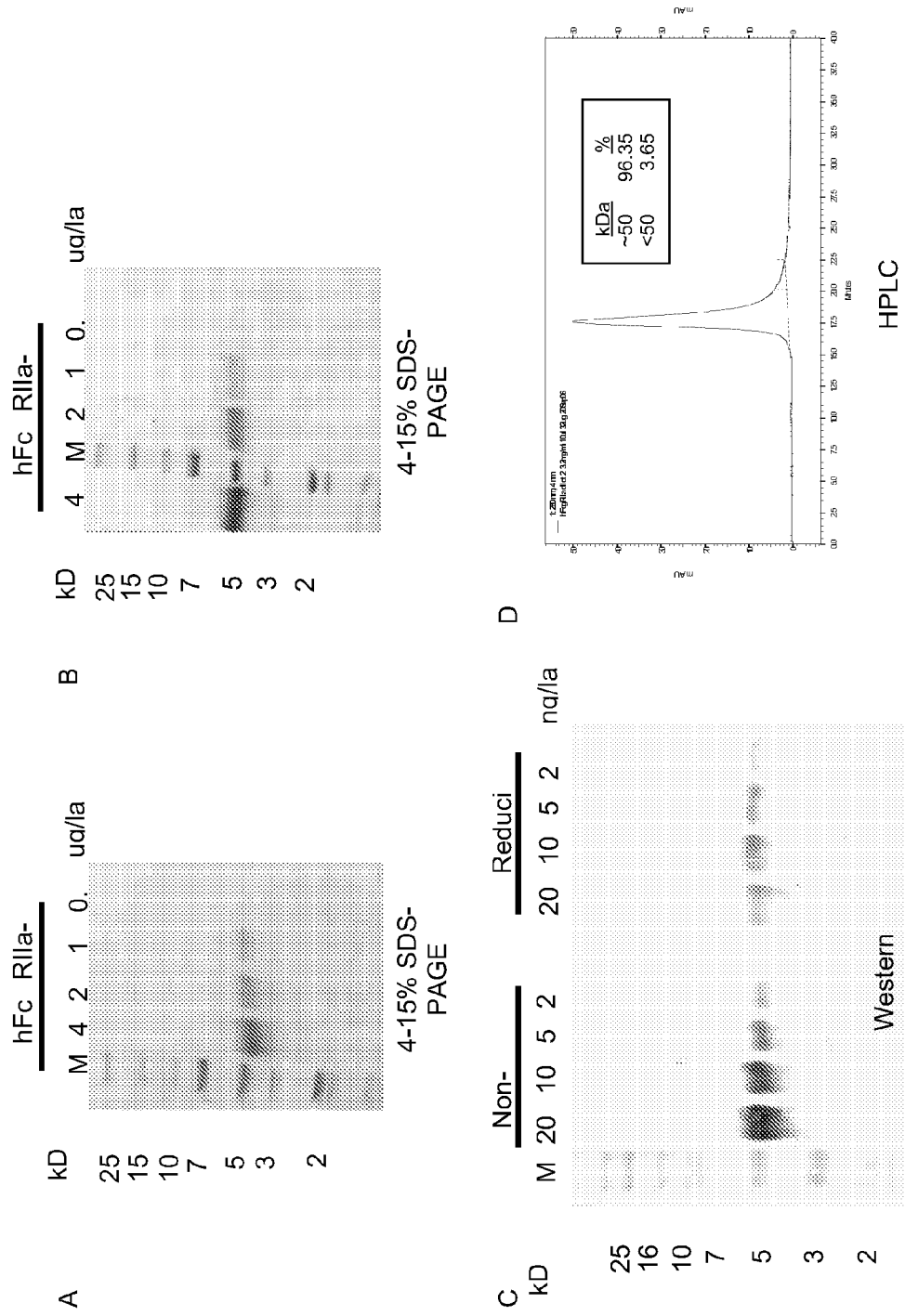
FIG. 10 provides results from the analysis of the rsFcγRIIa dimer isolated from stably transfected CHO—S cells by SDS-PAGE under (a) non-reducing and (b) reducing conditions, (c) Western blotting using an anti-FcγRIIa antibody, and (d) HPLC. The rsFcγRIIa dimer migrates as a single band at the expected molecular weight (~50 kD), reacts with anti-FcγRIIa antibody and was >96% pure as determined by HPLC analysis.

FIG. 10 shows the analysis of purified rsFcγRIIa material, including SDS-PAGE (under reducing and non-reducing conditions); Western blotting using an anti-FcγRIIa antibody (R&D systems, catalogue number AF1875) and rabbit anti-goat IgG-peroxidase as the detector antibody; and HPLC. The polypeptide migrates as a single band at the expected molecular weight (~50 kD), reacts with anti-FcγRIIa antibody and is >96% pure as determined by HPLC analysis.

rsFcγRIIa Dimer Polypeptides Block HAGG Binding to FcγRIIb

Figure 11:
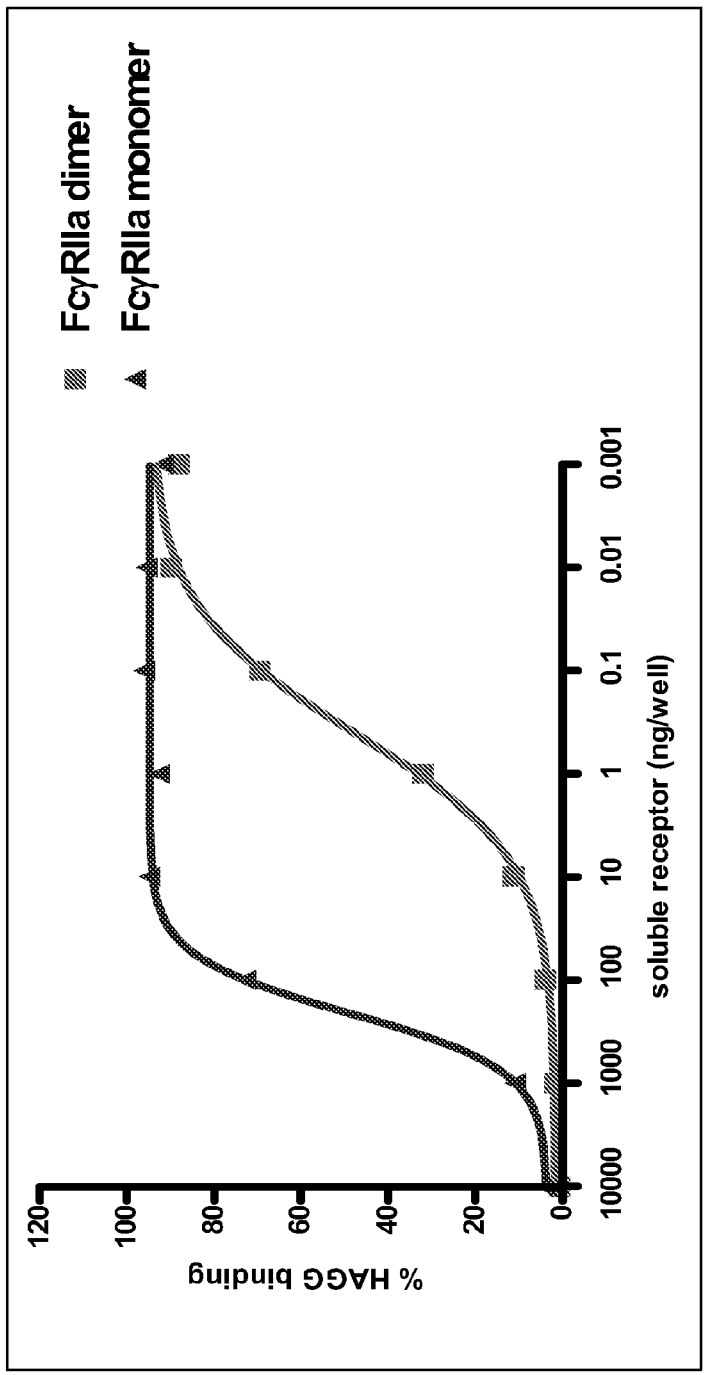
FIG. 11 provides a plot of immune-complex (HAGG) binding to cell surface-expressed human FcγRIIb (on the murine B lymphoma cell line IIA1.6) in the presence of either rsFcγRIIa monomer or rsFcγRIIa dimer.

The results of the HAGG binding assay are shown in FIG. 11. Both the rsFcγRIIa dimer and rsFcγRIIa monomer were able to completely block the binding of HAGG to cell surface FcγRIIb. However, the rsFcγRIIa dimer (IC50=3.9 ng/ml) was over 500-fold more potent than the monomer protein (IC50=2082 ng/ml).

rsFcγRIIa Dimer Polypeptides Block HAGG-Induced Platelet Activation

Figure 12:
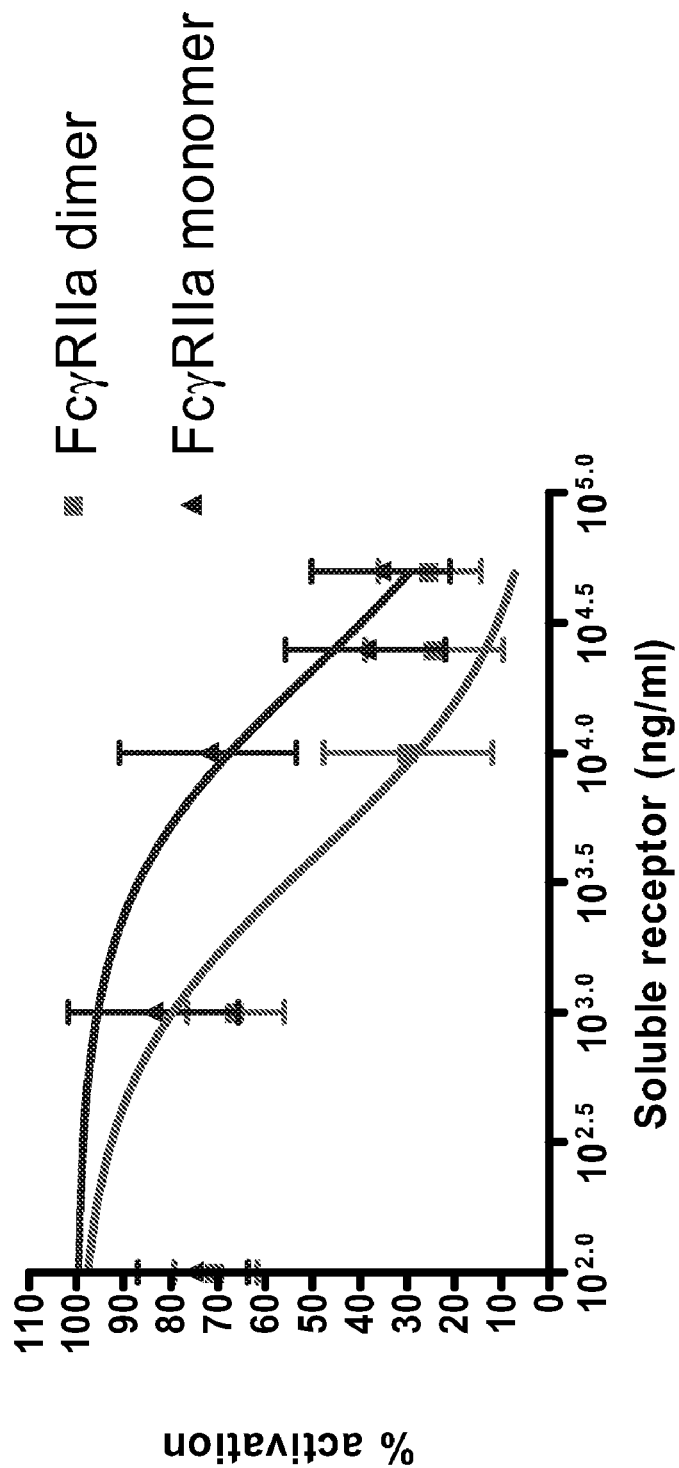
FIG. 12 provides a plot of activated platelets (positive for both CD41 and CD62P) after treatment with HAGG in the presence of rsFcγRIIa monomer or rsFcγRIIa dimer (expressed from the nucleotide sequence of FIG. 1), as a percentage of activated platelets following treatment with HAGG alone.

The results of the platelet activation assay are shown in FIG. 12. The percentage of activated platelets (positive for both CD41 and CD62P) after treatment with HAGG alone was defined as 100%. Both rsFcγRIIa dimer and rsFcγRIIa monomer were able to significantly reduce HAGG-induced CD62P upregulation. Titration revealed that the rsFcγRIIa dimer (IC50=3.9 µg/ml) was 5-fold more potent than the rsFcγRIIa monomer (IC50=20.9 µg/ml).

rsFcγRIIa Dimer Polypeptides Block Immune Complex-Induced MC/9 Activation

Figure 13:
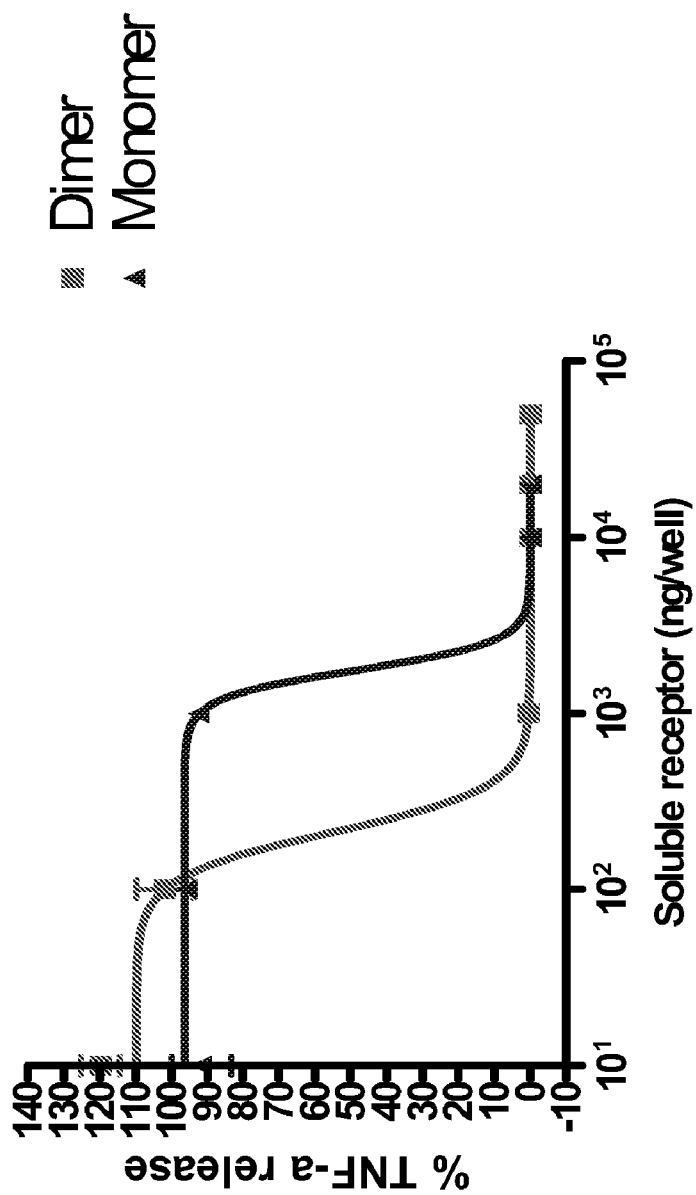
FIG. 13 provides a plot of TNF-α release from MC/9 cells after incubation with OVA immune complexes in the presence of rsFcγRIIa monomer or rsFcγRIIa dimer, as a percentage of TNF-α released in the presence of OVA immune complexes alone.

The results of the MC/9 activation assay are shown in FIG. 13. The amount of TNF-α released after incubation with OVA ICs alone was defined as 100%. Both rsFcγRIIa dimer and rsFcγRIIa monomer were able to completely suppress TNF-α release induced by immune complexes. Titration revealed that the rsFcγRIIa dimer (IC50=2.1 µg/ml) was 8-fold more potent than the rsFcγRIIa monomer (IC50=17.7 µg/ml).

rsFcγRIIa Dimer Inhibits Induced Arthritis in Human FcγRIIa Transgenic Mouse Model As shown in FIG. 18, the administration of the rsFcγRIIa dimer provided a dramatic reduction in arthritis score. A second experiment confirmed the reduction in arthritis score mediated by the dimer, albeit in less dramatic fashion.

Discussion

The rsFcγRIIa dimer was successfully expressed in CHO—S cells. Reducing and non-reducing SDS-PAGE showed that the purified rsFcγRIIa dimer was approximately 50 kDa in size, and Western blotting showed that the dimer was specifically bound by anti-FcγRIIa antibodies. The rsFcγRIIa dimer was determined to be 96% pure by HPLC.

Both the rsFcγRIIa dimer and rsFcγRIIa monomer completely blocked binding of HAGG to cell surface FcγRIIb, with the rsFcγRIIa dimer having an approximately 500-fold increased blocking efficiency than the rsFcγRIIa monomer. Similarly, both the rsFcγRIIa dimer and rsFcγRIIa monomer significantly reduced HAGG-induced platelet activation, with the dimer showing approximately 5-fold higher efficacy than the rsFcγRIIa monomer. Further, both the rsFcγRIIa dimer and rsFcγRIIa monomer suppressed mouse mast cell line (MC/9) activation, as measured by TNF-α release, with the dimer showing 8-fold greater efficacy than the monomer.

Importantly, the rsFcγRIIa dimer ameliorated arthritis in a mouse model of induced arthritis, demonstrating in vivo effectiveness.

Example 3

Engineering and Expression of rsFcγRIIa Fusion Polypeptides Comprising an Fc Domain Derived from $IgG_1$ Materials and Methods
Construction of rsFcγRIIa Fusion Expression Vectors Polynucleotides encoding soluble monomer FcγRIIa or soluble dimer FcγRIIa were independently fused to a polynucleotide encoding $IgG_1$-Fcγ1 (L234A, L235A).

The C-terminal of the soluble monomer FcγRIIa polypeptide was operably fused to a human $IgG_1$ polypeptide at a position on the N-terminal side of the inter-chain disulphide bond in the lower hinge that covalently joins the two Fc portions. Fusion at this position generates a monomeric FcγRIIa-$IgG_1$-Fcγ1 (L234A, L235A) fusion protein which will dimerise with a second Fc domain due to interactions present between covalently associated Fc domains. The IgG hinge region is known for its flexibility, and fusion of the polypeptide comprising the Fc binding region to the N-terminal side of the inter-chain disulphide bond in the lower hinge allows considerable freedom of movement of the Fc binding region.

Similarly, the C-terminal of the soluble dimer FcγRIIa polypeptide was operably fused to a human $IgG_1$ polypeptide at a position on the N-terminal side of the inter-chain disulphide bond in the lower hinge that covalently joins the two Fc portions.

Polynucleotides encoding soluble monomer FcγRIIa or soluble dimer FcγRIIa were independently fused to a polynucleotide encoding human serum albumin (HSA) in an equivalent manner to that previously described in International patent specification no WO 96/08512. As disclosed in that specification, the HSA was fused to the N-terminal of the rsFcγRIIa monomer. In a similar manner, the HSA was fused to the N-terminal of the rsFcγRIIa dimer.

Polynucleotides encoding the various fusion polypeptides or proteins were operably inserted into pAPEX 3P-xDEST using standard cloning techniques.

Production of rsFcγRIIa Monomer and rsFcγRIIa Dimer Fusions

The rsFcγRIIa monomer and dimer fusion expression vectors were transiently transfected into CHOP cells and stably transfected in 293E cells using standard methods. Transiently transfected CHOP cell supernatants were immunoprecipitated using anti-FcγRIIa antibody 8.2 (Powell et al., 1999) and immunoprecipitates were subjected to non-reducing SDS-PAGE (12%). Western blot analysis was then performed using standard methods and utilising rabbit anti FcγRIIa antibody (Maxwell et al., 1999) as a primary antibody and anti rabbit Ig-HRP as a secondary antibody.

HAGG-Capture ELISA for Detection of rsFcγRIIa Fusions in Transfected CHOP Cell Supernatants HAGG-capture ELISAs were performed to measure the Fc binding activity of the rsFcγRIIa fusions. To examine the binding activity of the rsFcγRIIa monomer fusions, a known FcγRIIa monomer standard (Powell et al., 1999) (starting at 0.75 μg) and the protein from an rsFcγRIIa monomer transfected cell (transfection 426) titrated and compared with the binding of protein from cells transfected with rsFcγRIIa monomer fusion to IgG-Fcγ1 (L234A, L235A) (monomer-Fc) and protein from cells transfected with rsFcγRIIa monomer fusion to HSA (HSA-monomer).

To examine the binding activity of rsFcγRIIa dimer fusions, a known FcγRIIa dimer standard (starting at 0.5 μg/ml) and protein from a cell transfected with rsFcγRIIa dimer (transfection 427) were titrated and compared with the binding of protein from cells transfected with rsFcγRIIa dimer fusion to IgG-Fcγ1 (L234A, L235A) (dimer-Fc) and protein from cells transfected with rsFcγRIIa dimer fusion to HSA (HSA-dimer).

Capture-Tag ELISA for Detection of rsFcγRIIa Fusions in Transfected CHOP Cell Supernatants Using a standard ELISA method, plates were coated with anti FcγRIIa antibody 8.2. The rsFcγRIIa fusions were added to the wells and contacted with the 8.2 antibody. The secondary antibody was anti FcγRIIa antibody 8.7-HRP (Powell et al., 1999; Ierino et al., 1993a), which is specific for a different FcγRIIa epitope than antibody 8.2.

The monomeric rsFcγRIIa samples tested included a known rsFcγRIIa monomer (monomer standard starting at 0.75 μg/ml), the supernatant from rsFcγRIIa monomer transfected cell (transfection 426), the supernatant from cells transfected with rsFcγRIIa monomer fusion to IgG-Fcγ1 (L234A, L235A) (monomer-Fc) and the supernatant from cells transfected with rsFcγRIIa monomer fusion to HSA (HSA-monomer).

The dimeric rsFcγRIIa samples tested included a known FcγRIIa dimer (dimer standard starting at 0.5 μg/ml), the supernatant from rsFcγRIIa dimer transfected cell (transfection 427), the supernatant from cells transfected with rsFcγRIIa dimer fusion to IgG-Fcγ1 (L234A, L235A) (monomer-Fc) and the supernatant from cells transfected with rsFcγRIIa dimer fusion to HSA (HSA-monomer).

Results
Expression of rsFcγRIIa Monomer and Dimer Fusions

On the basis of the activity of purified rsFcγRIIa monomer and rsFcγRIIa dimer, the rsFcγRIIa monomer-IgG-Fcγ1 (L234A, L235A) fusion was secreted at higher levels (approximately 12 μg/ml in 293E cells) than the rsFcγRIIa dimer-IgG-Fcγ1 (L234A, L235A) fusion (approximately 4 μg/ml in 293E cells).

Figure 14:
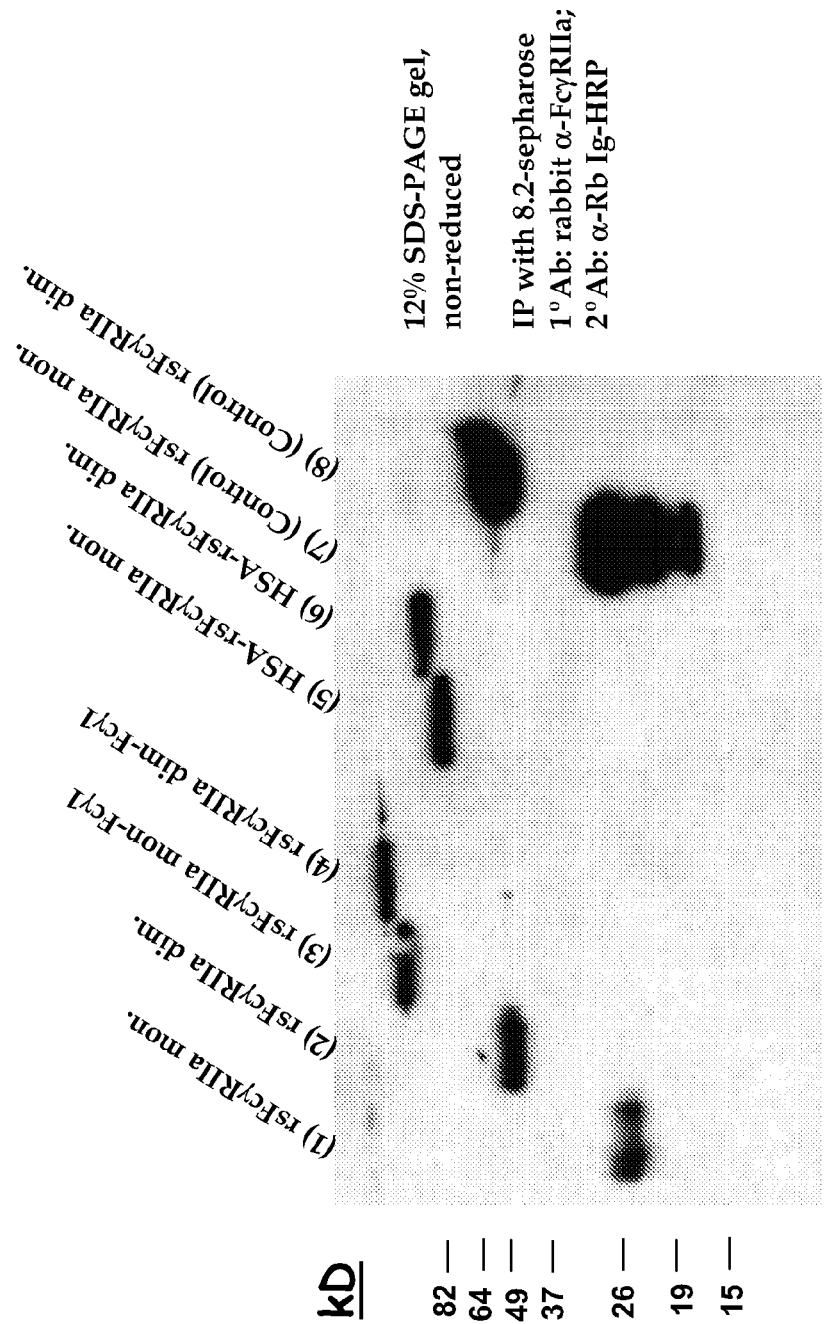
FIG. 14 shows Western blot analysis of rsFcγRIIa fusion proteins. (1) rsFcγRIIa monomer; (2) rsFcγRIIa dimer; (3) rsFcγRIIa monomer fused to IgG$_1$-Fcγ1 (L234A, L235A); (4) the rsFcγRIIa dimer fused to IgG$_1$-Fcγ1 (L234A, L235A); (5) rsFcγRIIa monomer fused to human serum albumin (HSA)

As shown in FIG. 14, Western blot analysis indicated that the fusion proteins were present in the supernatant at the expected molecular weight sizes and that they could be successfully produced as distinct proteins without evidence of degradation products.

HAGG-Capture ELISA for Detection of rsFcγRIIa Fusions in Transfected CHOP Cell Supernatants As shown in FIG. 15(a), rsFcγRIIa monomer fusion to IgG-Fcγ1 (L234A, L235A) (monomer-Fc) was detectably bound in the assay, while rsFcγRIIa monomer fusion to HSA (HSA-monomer) was observed to bind poorly. This result may be explained by the fact that the rsFcγRIIa monomer fusion to IgG-Fcγ1 (L234A, L235A) will be a dimer (of the Fc binding region) as a consequence of dimerisation between the heavy chains of the fused Fc domains whereas rsFcγRIIa monomer fusion to HSA remains monomeric for the Fc binding region.

As shown in FIG. 15(b), purified rsFcγRIIa dimer fusion to IgG-Fcγ1 (L234A, L235A) (dimer-Fc) showed binding activity similar to the dimer standard, and rsFcγRIIa dimer fusion to HSA (HSA-monomer) had detectable, but lower, binding activity. In this case, the rsFcγRIIa dimer fusion to IgG-Fcγ1 (L234A, L235A) was, due to dimerisation between the heavy chains of the fused Fc domains, tetrameric (or "tetravalent") for the Fc binding region, whereas rsFcγRIIa dimer fusion to HSA remains dimeric for the Fc binding region.

Capture-Tag ELISA for Detection of rsFcγRIIa Fusions in Transfected CHOP Cell Supernatants As shown in FIG. 16 (a), rsFcγRIIa monomer fusion to IgG-Fcγ1 (L234A, L235A) and the rsFcγRIIa monomer fusion to HSA are both captured and detectable in this assay. As shown in FIG. 16(b), rsFcγRIIa dimer fusion to IgG-Fcγ1 (L234A, L235A) and the rsFcγRIIa dimer fusion to HSA are also both captured and detectable in this assay. Clearly, both the 8.2 epitope used to capture these receptors and the 8.7 epitope used to detect the captured receptors are intact indicating correct folding of the fusions.

Discussion

The rsFcγRIIa monomer and rsFcγRIIa dimer fusion constructs were expressed from the vector p-APEX 3P-xDST and expressed transiently in CHOP cells and stably in 293E cells. The expressed fusions presented as distinct proteins on Western blot with no evidence of degradation products.

The rsFcγRIIa dimer fusion to IgG-Fcγ1 (L234A, L235A) may show lower expression levels than its monomeric counterpart. However, the expression level of rsFcγRIIa dimer fusion to HSA was nearly equivalent to the expression level of rsFcγRIIa monomer fusion to HSA, as determined by Western blot (FIG. 14), and therefore shows considerable promise as a means for large scale production of rsFcγRIIa dimer. Of interest, the rsFcγRIIa dimer fusions showed higher HAGG and anti-FcγRIIa antibody 8.2 binding activity than monomeric counterparts. As mentioned above, this may be explained by the fact that the rsFcγRIIa dimer fusions were dimeric or tetrameric (in the case of the rsFcγRIIa dimer fusion to IgG-Fcγ1 (L234A, L235A)) for the Fc binding region, and as a consequence, possessed a higher apparent binding affinity (avidity) because of this multi-valency. It is anticipated that tetrameric molecules may bind to immune complexes with such affinity that the binding will be substantially irreversible.

Example 4

Engineering and Expression of rsFcγRIIa Fusion Polypeptides Comprising an Fc Domain Derived from IgG2a In this example, rsFcγRIIa dimer fusion proteins were prepared using a mutated murine IgG2a Fc domain as a fusion partner. The dimer fusion protein was designated D2. The activity of this protein was compared with the rsFcγRIIa dimer lacking a fusion partner (as described in Example 1 and 2), and with a rsFcγRIIa monomer fusion protein, wherein the fusion partner was the mutated murine IgG2a Fc domain.

Design of Recombinant Soluble D2FcγRIIaFc (D2) Protein

The translated amino acid sequence (SEQ ID NO: 8) and nucleotide sequence (SEQ ID NO: 9) of the D2 protein are shown in FIGS. 19 and 20, respectively. The D2 protein consists of the native FcγRIIa signal sequence (amino acids 1-31), the extracellular domains of an FcγRIIa protein (amino acids 32-205), a short linker corresponding to the FcγRIIa membrane proximal stalk plus an additional valine residue (residues 206-214), a second FcγRIIa protein (residues 215-385), a repeat of the membrane proximal stalk linker (residues 386-393) and a mouse IgG2a Fc domain (hinge-CH2-CH3) region (residues 394-625). The IgG2a Fc domain contains the following four mutations, which were introduced to reduce Fc receptor binding and complement fixation: Leu-413 to Glu (corresponding to position 235 in the EU numbering system), Glu-496 to Ala (corresponding to EU position 318), Lys-498 to Ala (corresponding to EU position 320) and Lys-500 to Ala (corresponding to EU position 322).

Construction of the D2 Expression Vector

The cDNA encoding the signal peptide and extracellular domains of mutated human FcγRIIa was amplified by PCR using a previously constructed plasmid (FcγRIIa-d/pAPEX-dest) as a template and primers 1 and 4 as shown in Table 1. The mutated mouse IgG2a Fc region was amplified by PCR using a previously constructed plasmid (CD200IgG2aFc-d) as a template and primers 2 and 3 as shown in Table 2.

TABLE 2

Primers used for plasmid construction
(restriction enzyme sites are underlined)

| Primer | Sequence |
| --- | --- |
| 1. Mouse FcγRIIa Forward (SEQ ID NO: 10) | 5'GGGATATT<u>GCTAGC</u>GCCACCATGGAGACCCAAATG<sup>3'</sup> |
| 2. Mouse IgG2a Reverse (SEQ ID NO: 11) | 5'TATCTAG<u>ACCGGT</u>TATCATTTACCCGGAGTCCGGGAGAAGCTC<sup>3'</sup> |
| 3. FcγRIIa Di mIgG2a MidFor (SEQ ID NO: 12) | 5'AGCTCTTCACCCCCCAGAGGGCCCACAATCAAGCCCTGTCCTC<sup>3'</sup> |
| 4. FcγRIIa Di mIgG2a MidRev (SEQ ID NO: 13) | 5'GGCCCTCTGGGGGGTGAAGAGCTGCCCATGCTGG<sup>3'</sup> |

The FcγRIIa and mutated mouse IgG2a Fc PCR products were then amplified by overlapping PCR using primers 1 and 2. Amplification was carried out by using platinum Pfx DNA polymerase (Invitrogen), in 1 mM MgSO$_4$, 0.4 mM each dNTP, 20 pmol of each primer and 100 ng of template DNA under the following conditions: initial melting at 94° C. for 5 min, followed by 30 cycles consisting of 94° C. for 1.5 min, then 65° C. for 2 min, then 72° C. for 3 min. The reactions were then held at 72° C. for 10 min and cooled to 4° C. The reaction products were electrophoresed through 0.7% agarose gels and visualized with ethidium bromide. The DNA band of interest was excised and purified from agarose gel by using QIAquick Gel Extraction Kit (Qiagen). This purified PCR product was digested with NheI and AgeI restriction enzymes and purified using the Qiaquick PCR Purification Kit (Qiagen). The fragment was then ligated by T4 DNA ligase into the pMPG expression plasmid that had been similarly digested with NheI and AgeI. The ligation reaction (5 μl) was then transformed into 50 μl of competent *Escherichia coli* DH5a cells (Invitrogen) according the manufacture instructions. Transformants were spread on LB-agar plates containing 100 μg/ml ampicillin, followed by incubation at 37° C. for 16 hours. Plasmid DNA was purified from small-scale *E. coli* cultures by mini-prep, and the DNA sequence confirmed. A diagram of the resulting expression plasmid pMPG-D2 FcγRIIA-IgG 2a FC is shown in FIG. 21.

Generation of CHO Clones Expressing D2 pMPG-D2 FcγRIIa-IgG2aFc plasmid DNA was isolated from a large culture of *E. coli* using a plasmid Maxi kit (Qiagen), linearized by XbaI, and purified by using QIAGEN tips. CHO—S cells growing in serum-free chemically defined medium were transfected with the linearioed plasmid using Lipofectamine 2000 reagent. After 48 hours, the cells were transferred into 96-well plates at different concentrations (10000, 5000, or 2000 cells/well) in medium containing 600 μg/ml of hygromycin B. Drug-resistant oligoclones were screed by ELISA as follows: 96-well plates were coated with 100 μl of goat anti-mouse IgGFc (Sigma) and incubated overnight at 4° C. The wells were washed and blocked with 200 μl of 2% BSA in PBST at room temperature for 1 hour. After washing, 100 μl samples were diluted with 1% BSA in PBST, added to the wells, incubated for 1 hour, washed and then incubated with HRP-conjugated goat anti-mouse IgG (Fc specific) (Sigma) for 1 hour at room temperature. The wells were washed and TMB substrate added and incubated for 3 to 5 min at room temperature. Absorbance was measured at 450 nm, and a standard curve constructed using known amount of purified mouse IgG or D2 FcγRIIa-IgG2aFc. Supernatant samples were also analyzed by SDS-PAGE and Western blotting. For SDS-PAGE, samples were resuspended in sample buffer with or without 2-ME and heated at 95° C. for 10 min and chilled on ice. The samples were then separated on a 8% SDS-PAGE gel. The gel was then stained with Coomassie Blue according to the manufacture's instructions. For Western blotting, samples were prepared and separated on a SDS-PAGE as described above and then transferred onto ImmunoBlot PVDF Membrane (Bio-Rad) for 1 hr at 100V. The membrane was blocked for 1 hr in 5% skim milk in PBS/0.1% Tween-20 and incubated for 1 hr with 0.2 μg/ml goat anti-human FcγRIIa antibody (R&D Systems) and 1 hr with HRP-conjugated rabbit anti-goat IgG (whole molecule from Sigma), then developed using TMB substrate (Vector Laboratories Inc). A second limiting dilution was performed at lower different concentrations (0.25, and 0.5 cell/well) in medium containing 600 μg/ml of hygromycin B. After 2 to 3 weeks, the drug-resistant clones were again assessed for recombinant protein production by ELISA and tested by Western blot.

Purification of D2 Protein

CHO transfectants were grown in shaker flasks at 37° C. When the cells reached a density of 1.5 to $2 \times 10^6$ cells/ml, they were incubated at 30° C. for 7 to 10 days with constant agitation. Supernatant was collected, centrifuged at 3000×g for 30 min at 4° C., and filtered through a series of different autoclaved membrane filter pore sizes (5.0 to 0.2 μm). Tangential flow filtration (Millipore) using a BioMax 10 membrane was used to concentrate the supernatant and perform buffer exchange into 20 mM Na—P/148 mM NaCl, pH 7.8. The material was then diluted 9-fold with binding buffer (20 mM Na—P & 3 M NaCl, pH 7.8) and loaded onto a Protein A column (GE Heathcare) at 4 ml/min overnight at 4° C. The column was washed with binding buffer (20 volumes at 5 ml/min), and protein eluted with 0.1 M citric acid pH 4.0 at 2 ml/min. Eluted material was pH adjusted to neutral and dialyzed against 4 L of 10 mM Na—P, pH 6.0 at 4° C. overnight. It was then loaded onto a macro-prep 40 μm ceramic hydroxyapatite type II (CHT II) column, (Bio-Rad). After washing the column with binding buffer, the protein was eluted with 10 mM Na—P, 500 mM NaCl, pH 6.0 (all manipulations at a flow rate of 5 ml/min. The eluted material was then dialyzed against 3×4 L of PBS, pH 7.4 at 4° C.

Protein concentration was determined by absorbance at 280 nM (1.34 extinction coefficient). FIG. 22A shows the SDS-PAGE analysis of the final purified material. Western blot analysis is shown in FIG. 22B.

D2 Protein Blocks Immune Complex Induced MC/9 Mast Cell Activation

The D2 protein was tested for the ability to block immune complex-mediated activation of Fcγ receptors in a MC/9 mast cell assay. MC/9 is an FcγR-positive murine mast cell line that becomes activated and releases TNF-α after exposure to immune complexes. 10 μg of ovalbumin-anti-ovalbumin immune complexes (OVA ICs) were incubated with purified D2 for 1 hour at room temperature. OVA ICs were also incubated with purified BIF (a variant of D2 lacking an Fc tag as described in Examples 1 and 2) and purified M2 protein (a variant of D2 that contains only a single FcγRIIa subunit fused to the mutated IgG2a Fc domain). The mixture was then added to 96-well plates containing $2 \times 10^5$ MC/9 cells, and incubated overnight at 37° C. Supernatant was collected and the amount of TNF-α measured by commercial ELISA kit. The results are shown in FIG. 23, where the amount of TNF-α released in the absence of treatment has been defined as 100%. All three proteins completely suppress OVA IC-mediated activation. The D2 protein, however, is 3-fold more potent than the non-Fc tagged dimer, and 12-fold more potent than Fc-tagged monomer (M2).

D2 Protein Blocks Immune Complex Mediated Activation of FcγR in a Neutrophil Activation Assay The D2 protein was also tested for the ability to block immune complex-mediated activation of Fcγ receptors in a neutrophil activation assay. Resting human neutrophils express both FcγRIIa and FcγRIIIb and rapidly lose cell surface expression of L-selectin (CD62L) upon activation by immune complexes. OVA ICs (100 μg/ml) were incubated either alone or with titrated amount of purified D2, M2 or BIF for 1 hour on ice. The mixture was then added to 96-well plates containing $2 \times 10^5$/well human neutrophils, which had been purified from peripheral blood by dextran sedimentation and Ficoll density gradient centrifugation. The plates were incubated at 37° C. for 15 min, and the reaction terminated by addition of an equal volume of ice cold buffer followed by incubation on ice for 5 min. The level of CD62L on the neutrophil cell surface was then determined by flow cytometry. The results are shown in FIG. 24, where the percent of cells expressing CD62L in the presence of OVA IC alone is defined as 100% percent activation, and the percent of CD62L-expressing untreated cells as 0% activation. BIF and M2 protein showed similar suppressive activity. The D2 protein, however, is approximately 6-fold more potent.

D2 Protein Blocks Immune Complex Mediated Activation of FcγR in a Platelet Activation Assay In addition, the D2 protein was tested for the ability to block immune complex-mediated activation of Fc☐ receptors in a platelet activation assay. Exposure of platelets to heat aggregated IgG (HAGG), a typical immune complex, results in activation via FcγRIIa, leading to upregulation of P-selectin (CD62P). Heat aggregated IgG (HAGG) was incubated with various concentrations of D2 protein (or M2 or BIF) for 1 hour at 4° C. The mixture was then added to 96-well plates containing $3 \times 10^7$ human platelets, which had been previously washed and resuspended in Tyrodes/Hepes buffer supplemented with 1 mM EDTA. After a 30 minute incubation at room temperature the cells were washed, fixed, and stained for CD62P and GPIIb (CD41) expression by standard techniques and analyzed on a FACS Scan flow cytometer. The results of the activation assay are shown in FIG. 25. The percentage of activated platelets (positive for both CD41 and CD62P) after treatment with HAGG alone was defined as 100%. BIF and M2 protein showed similar suppressive activity. The D2 protein, however, is approximately 3-fold more potent.

Discussion

The D2 protein contains the extracellular domain of two head-to-tail FcγRIIa proteins fused to the murine IgG2a Fc domain, which is mutated at four amino acids to reduce Fc receptor binding and complement fixation. The D2 protein effectively blocked the immune complex mediated activation of MC/9 mast cells, and immune complex mediated activation of FcγR in both a neutrophil activation assay and a platelet activation assay. Such Fc binding dimer fusion proteins may accordingly be effective inhibitors of immune complex-mediated diseases in vivo.

Example 5

Engineering and Expression of Heterodimeric Fc Receptor Polypeptides

Materials and Methods
Construction of FcγRIIa-FcγRIII Heterodimeric Expression Vectors The Fc binding region of FcγRIIa and FcγRIII may be independently PCR amplified from cDNA template using appropriate primers as described in Example 1. The regions amplified would encompass the known characteristic residues and motifs of Fc binding regions such as residues of the ectodomain 1 and ectodomain 2 linker (i.e. the D1/D2 junction), and the BC, C'E and FG loops. The polynucleotide sequences for these Fc binding regions are well known to persons skilled in the art.

Blunt-ended PCR products can be ligated using T4 DNA ligase into the vector pPIC9 (Invitrogen, Life Technologies) at the EcoRI site filled in with Klenow fragment of DNA polymerase I. An operably fused FcγRIIa-FcγRIII heterodimeric polynucleotide may be created from these amplified products using similar PCR and cloning techniques as those described in Example 1. Insert size and orientation may be confirmed by analytical restriction enzyme digestion or DNA sequencing.

The operably fused FcγRIIa-FcγRIII heterodimeric polynucleotide can be cloned into various expression vectors. For example, the FcγRIIa-FcγRIII heterodimeric polynucleotide may be ligated into the EcoRI/XbaI sites of modified pBAC-PAK9 (Invitrogen Life Tech) in which the BamHI site in the multiple cloning site had first been eliminated by digest with BamHI, filling in using Klenow fragment of DNA polymerase and re-ligation. Insert sizes may be defined by EcoRI/XbaI digest and the correct orientation of the multimerising BamHI fragment can be screened by PvuII digest using standard protocols.

Alternatively, the FcγRIIa-FcγRIII heterodimeric polynucleotide can be cloned into mammalian expression vectors. For example, the Gateway LR clonase reaction (Invitrogen, Life Technologies) may be used to transfer operationally fused multimeric Fc receptor polynucleotide fragments into Gateway™ reading frame-A cassette (Invitrogen, Life Technologies) adapted expression vector pAPEX3P (Evans et al, 1995, and Christiansen et al., 1996) to give mammalian expression vectors expressing the fused Fc receptor multimers. Likewise, the Gateway LR clonase reaction can be used to transfer the operationally fused multimeric Fc receptor polynucleotide fragments into Gateway™ reading frame-A cassette (Invitrogen, Life Technologies) adapted expression vector pIRESneo (Clontech).

Discussion

Multimerisation of Fc binding regions generates molecules having higher avidity interactions with Fc domains. Each monomer in the multimer is able to separately interact with the Fc domain of immunoglobulins to give higher avidities. Multimers containing Fc binding domains derived from different Fc receptors may be generated. For example, multimers could be formed from combinations of the Fc binding regions of FcγRI, FgγRIIa, FcγRIIb, FcγRIIIa, FcγRIIIb, FcαRI and FcεRI. Heterodimers could also be formed from combinations of these Fc binding regions. For example, FcγRIIa-FcγRIII, FcγRIIa-FcγRI, and FcγRI-FcγRIII heterodimers could be formed, as well as heterodimers consisting of other combinations of Fc binding regions.

The Fc binding domains of a number of Fc receptors have been defined by mutagenesis or crystallography (IgG and FcγR: Maxwell et al. 1999, Radaev et al., 2001, Sondermann et al., 2000, Hulett et al., 1988, Hulett et al., 1991, Hulett et al., 1994, Hulett et al., 1995; IgE and FcεRI: Garman et al., 2000; IgA and FcαRI interactions: Wines et al., 2001, Herr et al., 2003). Further, comparisons of similar FcR sequences and comparative analysis of Fc receptor structures have been made (Sondermann et al., 2001). These analyses show that related, clearly defined segments of different Fc receptors are capable of interacting with their ligands. Moreover, crystallographic analysis has demonstrated this clearly for the FcγRIIa and IgG interaction in International patent application no PCT/AU2006/000813 compared to crystallographic analyses of FcγRIII and IgG (Radaev et al. 2001, Sonderman et al., 2001).

It is clear that these data together with mutagenesis experiments of other Fc receptors indicate that segments from the connecting region between ectodomain 1 and ectodomain 2 of these related Fc receptors, as well as segments from the BC, C'E and FG loops of the second domains of different receptors, interact with their respective ligands. Incorporation of such Fc binding regions into other polypeptides could confer specificity for that immunoglobulin type on the new polypeptide. To this end, Hulett et al., 1991, Hulett et al., 1995, and Maxwell et al., 1999 have demonstrated that the addition of IgG binding regions into proteins that were otherwise unable to bind IgG acquired specificity for IgG. Similarly, it has been observed that the insertion of a series of IgE binding sequences into proteins unable to bind IgE resulted in protein chimaeras with IgE specificity as previously described in WO 96/08512. It can therefore be predicted that in a similar manner, the inclusion of Fc binding regions that interact with IgG from FcγRI or FcγRIII into a protein could confer IgG binding function to that protein, or similarly, the inclusion of Fc binding regions that interact with IgA from CD89 or FcαRI into a protein could confer IgA binding function to that protein. Such sequences could include the loops of the first extracellular domain of FcαRI of CD89 that are known to interact with IgA, such loops would include the BC, C'E and FG loops of domain 1. Important residues include amino acids 35, 52 and 81-86 (Wines et al., 2001, Herr et al., 2003). In this way, receptor proteins or peptides containing segments capable of interacting with different classes of immunoglobulins are possible.

Throughout this specification the word "comprise", or variations such as "comprises" or comprising, will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Amirahmadi S F et al. & Rowley M J. 2005. Arthritogenic anti-type II collagen antibodies are pathogenic for cartilage-derived chondrocytes independent of inflammatory cells. *Arthritis Rheum.* 52(6):1897-906.
2. Armour K L et al. & Clark M R. 2003. Differential binding to human FcgammaRIIa and FcgammaRIIb receptors by human IgG wildtype and mutant antibodies. *Mol. Immunol.* 40(9):585-93.
3. Armour K L et al. & Clark M R. 2002. The contrasting IgG-binding interactions of human and herpes simplex virus Fc receptors. *Biochem Soc Trans.* 30(4):495-500.
4. Astier A et al. & D Hanau. 1994. Human epidermal Langerhans cells secrete a soluble receptor for IgG (Fc gamma RII/CD32) that inhibits the binding of immune complexes to Fc gamma R+ cells. *J Immunol.* 152(1):201.
5. Christiansen D et al. & B E Loveland. 1996. Engineering of recombinant soluble CD46: an inhibitor of complement activation. *Immunology.* 87:348.
6. Emery P et al. & G Seydoux. 2001. *Rheumatology (Oxford)* 40:699.
7. Evans M J et al. & S P Squinto. 1995. Rapid expression of an anti-human C5 chimeric Fab utilizing a vector that replicates in COS and 293 cells. *J Immunol Methods.* 1995 184:123.
8. Garman S C et al., 2000. Structure of the Fc fragment of human IgE bound to its high-affinity receptor Fc epsilonRI alpha. *Nature* 406(6793):259-66.
9. Herr A B et al., 2003. Insights into IgA-mediated immune responses from the crystal structures of human FcalphaRI and its complex with IgA1-Fc. *Nature* 423(6940):614-20.
10. Hibbs M L et al. & P M Hogarth. 1988. Molecular cloning of a human immunoglobulin G Fc receptor. *Proc Natl Acad Sci USA* 85 (7), 2240.
11. Hulett M D et al. & P M Hogarth. 1991. Chimeric Fc receptors identify functional domains of the murine high affinity receptor for IgG. *J Immunol.* 47(6):1863-8.
12. Hulett M D et al. & P M Hogarth. 1994. Identification of the IgG binding site of the human low affinity receptor for IgG Fc gamma RII. Enhancement and ablation of binding by site-directed mutagenesis. *J Biol. Chem.* 269(21):15287.
13. Hulett M D et al. & P M Hogarth. 1995. Multiple regions of human Fc gamma RII (CD32) contribute to the binding of IgG. *J Biol. Chem.* 270(36):21188.
14. Hulett M D & P M Hogarth. 1998. The second and third extracellular domains of FcgammaRI (CD64) confer the unique high affinity binding of IgG2a. *Mol. Immunol.* 35(14-15):989.
15. Ierino F L et al. & P M Hogarth. 1993a. Rec. soluble human FcγRII: prodn, characterization, and inhibition of the Arthus reaction. *J Exp Med* 178:1617.
16. Ierino F L et al. & P M Hogarth. 1993b. Mapping epitopes of human Fc gamma RII (CDw32) with monoclonal antibodies and recombinant receptors. *J. Immunol.* 150:1794-803.
17. Lau L M et al. & D E Jackson. 2004. The tetraspanin superfamily member CD151 regulates outside-in integrin alphaIIbbeta 3 signaling and platelet function. *Blood.* 104 (8):2368.
18. Maxwell K F et al. & P M Hogarth. 1999. Crystal structure of the human leukocyte Fc receptor, Fc gammaRIIa. *Nat Struct Biol* 6:437.
19. Nabbe K C et al. & W B van den Berg. 2003. Coordinate expression of activating Fc gamma receptors I and III and inhibiting Fc gamma receptor type II in the determination of joint inflammation and cartilage destruction during immune complex-mediated arthritis. *Arthritis Rheum* 48:255.
20. Nandakumar K S et al. & Holmdahl R. 2004. Collagen type II (CII)-specific antibodies induce arthritis in the absence of T or B cells but the arthritis progression is enhanced by CII-reactive T cells. *Arthritis Res Ther.* 6(6): R544-50.
21. Pflum L R & M L Graeme. 1979. The Arthus reaction in rats, a possible test for anti-inflammatory and anti-rheumatic drugs. *Agents Actions* 9:184.
22. Powell M S et al. & P M Hogarth. 1999. Biochemical analysis and crystallisation of Fc gamma RIIa, the low affinity receptor for IgG. *Immunol Lett.* 68(1):17.
23. Radaev S et al., 2001. The structure of a human type III Fcgamma receptor in complex with Fc. *J. Biol. Chem.* 276(19):16469-77.
24. Sondermann P et al., 2000. The 3.2-A crystal structure of the human IgG1 Fc fragment-Fc gammaRIII complex. *Nature* 406(6793):267-73.
25. Sondermann P et al., 2001. Molecular basis for immune complex recognition: a comparison of Fc-receptor structures. *J. Mol. Biol.* 309(3):737-49.
26. Takai T. 2002. Roles of Fc receptors in autoimmunity. *Nat Rev Immunol.* 2(8):580.
27. Tamm A et al. & R E Schmidt R E. 1996. The IgG binding site of human FcgammaRIIIB receptor involves CC' and FG loops of the membrane-proximal domain. *J Biol Chem.* 271(7):3659.
28. Thai LeM et al. & D E Jackson. 2003. Physical proximity and functional interplay of PECAM-1 with the Fc receptor Fc gamma RIIa on the platelet plasma membrane. *Blood.* 102(10):3637.
29. Wines B D & S B Easterbrook-Smith. 1988. Enhancement of the binding of C1q to immune complexes by polyethylene glycol. *Mol. Immunol.* 25(3):263.
30. Wines B D et al. & P M Hogarth. 2000. The IgG Fc contains distinct Fc receptor (FcR) binding sites: the leukocyte receptors Fc gamma RI and Fc gamma RIIa bind to a region in the Fc distinct from that recognized by neonatal FcR and protein A. *J. Immunol.* 164:5313-8

31. Wines B D et al. & P M Hogarth. 2001. The interaction of Fc alpha RI with IgA and its implications for ligand binding by immunoreceptors of the leukocyte receptor cluster. *J Immunol.* 166(3):1781.

32. Wines B D et al. & P M Hogarth. 2003. Soluble FcgammaRIIa inhibits rheumatoid factor binding to immune complexes. *Immunology.* 109(2):246.

33. Wright J K et al. & J C Jaton. 1980. Preparation and characterization of chemically defined oligomers of rabbit immunoglobulin G molecules for the complement binding studies. *Biochem J.* 187(3):767.

The invention claimed is:

1. A soluble multimeric protein or polypeptide able to inhibit interaction of leukocyte Fcγ receptors (FcγR) and immunoglobulin G (IgG), said protein or polypeptide consisting of:
   i) two linked Fc binding regions derived from an FcγR type receptor, wherein said Fc binding regions are linked in a head to tail arrangement; and
   ii) optionally a linker, wherein said Fc binding regions are linked through the optional linker and wherein said linker comprises from 1 to 20 amino acids;
   iii) optionally an amino acid tag motif,
   and wherein none of said linked Fc binding regions is fused to an Fc region of an immunoglobulin.

2. The protein or polypeptide of claim 1, wherein at least one Fc binding region derived from an FcγR type receptor is derived from an FcγRII type receptor.

3. The protein or polypeptide of claim 1, wherein at least one Fc binding region is derived from FcγRIIa.

4. The protein or polypeptide of claim 2, wherein each of said linked Fc binding regions is derived from the same FcγRII type receptor.

5. A soluble multimeric protein or polypeptide able to inhibit interaction of leukocyte Fcγ receptors (FcγR) and immunoglobulin G (IgG), said protein or polypeptide consisting of:
   i) two linked Fc binding regions derived from an FcγR type receptor, wherein said Fc binding regions are linked in a head to tail arrangement; and
   ii) optionally an amino acid tag motif.

6. A method of treating a subject for an immune-complex (IC)-mediated inflammatory disease, said method comprising administering to said subject the protein or polypeptide of claim 1 optionally in combination with a pharmaceutically- or veterinary-acceptable carrier or excipient.

7. The method of claim 6, wherein said IC-mediated inflammatory disease is selected from the group consisting of rheumatoid arthritis (RA), immune thrombocytopenic purpura (ITP), systemic lupus erythematosus (SLE), glomerulonephritis and heparin-induced tlu-ombocytopenia thrombosis syndrome (HITTS).

8. A method of removing circulating immune complexes (IC) from a subject suffering an immune-complex-mediated inflammatory disease, said method comprising the following steps:

(i) providing a protein or polypeptide according to claim 1 bound to a suitable substrate,
(ii) treating blood removed from said subject by contacting the blood ex vivo with said substrate-bound protein or polypeptide such that IC present in said blood is bound to the substrate via said protein or polypeptide,
(iii) separating the treated blood from the substrate, and
(iv) thereafter returning the treated blood to the subject.

* * * * *

SEQUENCE LISTING

```
<160> NUMBER OF SEQ ID NOS: 13

<210> SEQ ID NO 1
<211> LENGTH: 19
<212> TYPE: DNA
<213> ORGANISM: Homo sapiens

<400> SEQUENCE: 1
gtagctcccc caaaggctg                                                   19

<210> SEQ ID NO 2
<211> LENGTH: 25
<212> TYPE: DNA
<213> ORGANISM: Homo sapiens

<400> SEQUENCE: 2
ctacccgggt gaagagctgc ccatg                                            25

<210> SEQ ID NO 3
<211> LENGTH: 48
<212> TYPE: DNA
<213> ORGANISM: Homo sapiens

<400> SEQUENCE: 3
tctcatcacc accatcacca cgtctagacc cagctttctt gtacaaag                   48

<210> SEQ ID NO 4
<211> LENGTH: 10
<212> TYPE: PRT
<213> ORGANISM: Artificial
<220> FEATURE:
<223> OTHER INFORMATION: Synthetic linker

<400> SEQUENCE: 4

Gly Gly Gly Gly Ser Gly Gly Gly Gly Ser
1               5                   10

<210> SEQ ID NO 5
<211> LENGTH: 1206
<212> TYPE: DNA
<213> ORGANISM: Homo sapiens

<400> SEQUENCE: 5
atggagaccc aaatgtctca gaatgtatgt cccagaaacc tgtggctgct tcaaccattg      60
acagttttgc tgctgctggc ttctgcagac agtcaagctg cagctccccc aaaggctgtg     120
ctgaaacttg agccccgtg gatcaacgtg ctccaggagg actctgtgac tctgacatgc     180 caggggctc gcagccctga gagcgactcc attcagtggt tccacaatgg gaatctcatt     240
cccacccaca cgcagcccag ctacaggttc aaggccaaca caatgacag cggggagtac     300 acgtgccaga ctggccagac cagcctcagc gaccctgtgc atctgactgt gctttccgaa     360
tggctggtgc tccagacccc tcacctggag ttccaggagg agaaaccat catgctgagg     420 tgccacagct ggaaggacaa gcctctggtc aaggtcacat tcttccagaa tggaaaatcc     480
```

-continued

```
cagaaattct cccatttgga tcccaccttc tccatcccac aagcaaacca cagtcacagt    540
ggtgattacc actgcacagg aaacataggc tacacgctgt tctcatccaa gcctgtgacc    600
atcactgtcc aagtgcccag catgggcagc tcttcacccg tagctccccc aaaggctgtg    660
ctgaaacttg agccccgtg gatcaacgtg ctccaggagg actctgtgac tctgacatgc    720
caggggctc gcagccctga gagcgactcc attcagtggt tccacaatgg aatctcatt    780
cccacccaca cgcagcccag ctacaggttc aaggccaaca acaatgacag cggggagtac    840
acgtgccaga ctggccagac cagcctcagc gaccctgtgc atctgactgt gctttccgaa    900
tggctggtgc tccagacccc tcacctggag ttccaggagg agaaaccat catgctgagg    960
tgccacagct ggaaggacaa gcctctggtc aaggtcacat tcttccagaa tggaaaatcc   1020
cagaaattct cccatttgga tcccaccttc tccatcccac aagcaaacca cagtcacagt   1080
ggtgattacc actgcacagg aaacataggc tacacgctgt tctcatccaa gcctgtgacc   1140
atcactgtcc aagtgcccag catgggcagc tcttcaccct ctcatcacca ccatcaccac   1200
gtctag                                                              1206
```

<210> SEQ ID NO 6
<211> LENGTH: 401
<212> TYPE: PRT
<213> ORGANISM: Homo sapiens

<400> SEQUENCE: 6

```
Met Glu Thr Gln Met Ser Gln Asn Val Cys Pro Arg Asn Leu Trp Leu
1               5                   10                  15

Leu Gln Pro Leu Thr Val Leu Leu Leu Leu Ala Ser Ala Asp Ser Gln
                20                  25                  30

Ala Ala Ala Pro Pro Lys Ala Val Leu Lys Leu Glu Pro Pro Trp Ile
            35                  40                  45

Asn Val Leu Gln Glu Asp Ser Val Thr Leu Thr Cys Gln Gly Ala Arg
        50                  55                  60

Ser Pro Glu Ser Asp Ser Ile Gln Trp Phe His Asn Gly Asn Leu Ile
65                  70                  75                  80

Pro Thr His Thr Gln Pro Ser Tyr Arg Phe Lys Ala Asn Asn Asn Asp
                85                  90                  95

Ser Gly Glu Tyr Thr Cys Gln Thr Gly Gln Thr Ser Leu Ser Asp Pro
            100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
    130                 135                 140

Lys Asp Lys Pro Leu Val Lys Val Thr Phe Phe Gln Asn Gly Lys Ser
145                 150                 155                 160

Gln Lys Phe Ser His Leu Asp Pro Thr Phe Ser Ile Pro Gln Ala Asn
                165                 170                 175

His Ser His Ser Gly Asp Tyr His Cys Thr Gly Asn Ile Gly Tyr Thr
            180                 185                 190

Leu Phe Ser Ser Lys Pro Val Thr Ile Thr Val Gln Val Pro Ser Met
        195                 200                 205

Gly Ser Ser Ser Pro Val Ala Pro Lys Ala Val Leu Lys Leu Glu
    210                 215                 220

Pro Pro Trp Ile Asn Val Leu Gln Glu Asp Ser Val Thr Leu Thr Cys
225                 230                 235                 240
```

```
Gln Gly Ala Arg Ser Pro Glu Ser Asp Ser Ile Gln Trp Phe His Asn
                245                 250                 255

Gly Asn Leu Ile Pro Thr His Thr Gln Pro Ser Tyr Arg Phe Lys Ala
            260                 265                 270

Asn Asn Asn Asp Ser Gly Glu Tyr Thr Cys Gln Thr Gly Gln Thr Ser
            275                 280                 285

Leu Ser Asp Pro Val His Leu Thr Val Leu Ser Glu Trp Leu Val Leu
    290                 295                 300

Gln Thr Pro His Leu Glu Phe Gln Glu Gly Glu Thr Ile Met Leu Arg
305                 310                 315                 320

Cys His Ser Trp Lys Asp Lys Pro Leu Val Lys Val Thr Phe Phe Gln
                325                 330                 335

Asn Gly Lys Ser Gln Lys Phe Ser His Leu Asp Pro Thr Phe Ser Ile
            340                 345                 350

Pro Gln Ala Asn His Ser His Ser Gly Asp Tyr His Cys Thr Gly Asn
            355                 360                 365

Ile Gly Tyr Thr Leu Phe Ser Ser Lys Pro Val Thr Ile Thr Val Gln
    370                 375                 380

Val Pro Ser Met Gly Ser Ser Pro Ser His His His His His His
385                 390                 395                 400

Val

<210> SEQ ID NO 7
<211> LENGTH: 8
<212> TYPE: PRT
<213> ORGANISM: Homo sapiens

<400> SEQUENCE: 7

Pro Ser Met Gly Ser Ser Ser Pro
1               5

<210> SEQ ID NO 8
<211> LENGTH: 625
<212> TYPE: PRT
<213> ORGANISM: Artificial
<220> FEATURE:
<223> OTHER INFORMATION: Recombinant human and murine sequence

<400> SEQUENCE: 8

Met Glu Thr Gln Met Ser Gln Asn Val Cys Pro Arg Asn Leu Trp Leu
1               5                   10                  15

Leu Gln Pro Leu Thr Val Leu Leu Leu Leu Ala Ser Ala Asp Ser Gln
                20                  25                  30

Ala Ala Ala Pro Pro Lys Ala Val Leu Lys Leu Glu Pro Pro Trp Ile
            35                  40                  45

Asn Val Leu Gln Glu Asp Ser Val Thr Leu Thr Cys Gln Gly Ala Arg
        50                  55                  60

Ser Pro Glu Ser Asp Ser Ile Gln Trp Phe His Asn Gly Asn Leu Ile
65                  70                  75                  80

Pro Thr His Thr Gln Pro Ser Tyr Arg Phe Lys Ala Asn Asn Asn Asp
                85                  90                  95

Ser Gly Glu Tyr Thr Cys Gln Thr Gly Gln Thr Ser Leu Ser Asp Pro
            100                 105                 110

Val His Leu Thr Val Leu Ser Glu Trp Leu Val Leu Gln Thr Pro His
        115                 120                 125

Leu Glu Phe Gln Glu Gly Glu Thr Ile Met Leu Arg Cys His Ser Trp
    130                 135                 140
```

-continued

Lys Asp Lys Pro Leu Val Lys Val Thr Phe Phe Gln Asn Gly Lys Ser
145                 150                 155                 160

Gln Lys Phe Ser His Leu Asp Pro Thr Phe Ser Ile Pro Gln Ala Asn
            165                 170                 175

His Ser His Ser Gly Asp Tyr His Cys Thr Gly Asn Ile Gly Tyr Thr
        180                 185                 190

Leu Phe Ser Ser Lys Pro Val Thr Ile Thr Val Gln Val Pro Ser Met
    195                 200                 205

Gly Ser Ser Ser Pro Val Ala Pro Pro Lys Ala Val Leu Lys Leu Glu
210                 215                 220

Pro Pro Trp Ile Asn Val Leu Gln Glu Asp Ser Val Thr Leu Thr Cys
225                 230                 235                 240

Gln Gly Ala Arg Ser Pro Glu Ser Asp Ser Ile Gln Trp Phe His Asn
            245                 250                 255

Gly Asn Leu Ile Pro Thr His Thr Gln Pro Ser Tyr Arg Phe Lys Ala
        260                 265                 270

Asn Asn Asn Asp Ser Gly Glu Tyr Thr Cys Gln Thr Gly Gln Thr Ser
    275                 280                 285

Leu Ser Asp Pro Val His Leu Thr Val Leu Ser Glu Trp Leu Val Leu
290                 295                 300

Gln Thr Pro His Leu Glu Phe Gln Glu Gly Glu Thr Ile Met Leu Arg
305                 310                 315                 320

Cys His Ser Trp Lys Asp Lys Pro Leu Val Lys Val Thr Phe Phe Gln
            325                 330                 335

Asn Gly Lys Ser Gln Lys Phe Ser His Leu Asp Pro Thr Phe Ser Ile
        340                 345                 350

Pro Gln Ala Asn His Ser His Ser Gly Asp Tyr His Cys Thr Gly Asn
    355                 360                 365

Ile Gly Tyr Thr Leu Phe Ser Ser Lys Pro Val Thr Ile Thr Val Gln
    370                 375                 380

Val Pro Ser Met Gly Ser Ser Ser Pro Pro Arg Gly Pro Thr Ile Lys
385                 390                 395                 400

Pro Cys Pro Pro Cys Lys Cys Pro Ala Pro Asn Leu Glu Gly Gly Pro
            405                 410                 415

Ser Val Phe Ile Phe Pro Pro Lys Ile Lys Asp Val Leu Met Ile Ser
        420                 425                 430

Leu Ser Pro Ile Val Thr Cys Val Val Asp Val Ser Glu Asp Asp
    435                 440                 445

Pro Asp Val Gln Ile Ser Trp Phe Val Asn Asn Val Glu Val His Thr
450                 455                 460

Ala Gln Thr Gln Thr His Arg Glu Asp Tyr Asn Ser Thr Leu Arg Val
465                 470                 475                 480

Val Ser Ala Leu Pro Ile Gln His Gln Asp Trp Met Ser Gly Lys Ala
            485                 490                 495

Phe Ala Cys Ala Val Asn Asn Lys Asp Leu Pro Ala Pro Ile Glu Arg
        500                 505                 510

Thr Ile Ser Lys Pro Lys Gly Ser Val Arg Ala Pro Gln Val Tyr Val
    515                 520                 525

Leu Pro Pro Pro Glu Glu Glu Met Thr Lys Lys Gln Val Thr Leu Thr
530                 535                 540

Cys Met Val Thr Asp Phe Met Pro Glu Asp Ile Tyr Val Glu Trp Thr
545                 550                 555                 560

Asn Asn Gly Lys Thr Glu Leu Asn Tyr Lys Asn Thr Glu Pro Val Leu
            565                 570                 575

```
Asp Ser Asp Gly Ser Tyr Phe Met Tyr Ser Lys Leu Arg Val Glu Lys
                580                 585                 590
Lys Asn Trp Val Glu Arg Asn Ser Tyr Ser Cys Ser Val Val His Glu
            595                 600                 605
Gly Leu His Asn His His Thr Thr Lys Ser Phe Ser Arg Thr Pro Gly
        610                 615                 620
Lys
625

<210> SEQ ID NO 9
<211> LENGTH: 1899
<212> TYPE: DNA
<213> ORGANISM: Artificial
<220> FEATURE:
<223> OTHER INFORMATION: Recombinant human and and murine sequence

<400> SEQUENCE: 9
```

| | | | | | |
|---|---|---|---|---|---|
| gctagcgcca | ccatggagac | ccaaatgtct | cagaatgtat | gtcccagaaa | cctgtggctg | 60 |
| cttcaaccat | tgacagtttt | gctgctgctg | gcttctgcag | acagtcaagc | tgcagctccc | 120 |
| ccaaaggctg | tgctgaaact | tgagccccg | tggatcaacg | tgctccagga | ggactctgtg | 180 |
| actctgacat | gccagggggc | tcgcagccct | gagagcgact | ccattcagtg | gttccacaat | 240 |
| gggaatctca | ttcccaccca | cacgcagccc | agctacaggt | tcaaggccaa | caacaatgac | 300 |
| agcggggagt | acacgtgcca | gactggccag | accagcctca | gcgaccctgt | gcatctgact | 360 |
| gtgctttccg | aatggctggt | gctccagacc | cctcacctgg | agttccagga | gggagaaaac | 420 |
| atcatgctga | ggtgccacag | ctggaaggac | aagcctctgg | tcaaggtcac | attcttccag | 480 |
| aatggaaaat | cccagaaatt | ctcccatttg | gatcccacct | tctccatccc | acaagcaaac | 540 |
| cacagtcaca | gtggtgatta | ccactgcaca | ggaaacatag | gctacacgct | gttctcatcc | 600 |
| aagcctgtga | ccatcactgt | ccaagtgccc | agcatgggca | gctcttcacc | cgtagctccc | 660 |
| ccaaaggctg | tgctgaaact | tgagccccg | tggatcaacg | tgctccagga | ggactctgtg | 720 |
| actctgacat | gccagggggc | tcgcagccct | gagagcgact | ccattcagtg | gttccacaat | 780 |
| gggaatctca | ttcccaccca | cacgcagccc | agctacaggt | tcaaggccaa | caacaatgac | 840 |
| agcggggagt | acacgtgcca | gactggccag | accagcctca | gcgaccctgt | gcatctgact | 900 |
| gtgctttccg | aatggctggt | gctccagacc | cctcacctgg | agttccagga | gggagaaaac | 960 |
| atcatgctga | ggtgccacag | ctggaaggac | aagcctctgg | tcaaggtcac | attcttccag | 1020 |
| aatggaaaat | cccagaaatt | ctcccatttg | gatcccacct | tctccatccc | acaagcaaac | 1080 |
| cacagtcaca | gtggtgatta | ccactgcaca | ggaaacatag | gctacacgct | gttctcatcc | 1140 |
| aagcctgtga | ccatcactgt | ccaagtgccc | agcatgggca | gctcttcacc | ccccagaggg | 1200 |
| cccacaatca | agccctgtcc | tccatgcaaa | tgcccagcac | ctaacctcga | gggtggacca | 1260 |
| tccgtcttca | tcttccctcc | aaagatcaag | gatgtactca | tgatctccct | gagccccata | 1320 |
| gtcacatgtg | tggtggtgga | tgtgagcgag | gatgacccag | atgtccagat | cagctggttt | 1380 |
| gtgaacaacg | tggaagtaca | cacagctcag | acacaaaccc | atagagagga | ttacaacagt | 1440 |
| actctccggg | tggtcagtgc | cctccccatc | cagcaccagg | actggatgag | tggcaaggca | 1500 |
| ttcgcatgcg | cagtcaacaa | caaagacctc | ccagcgccca | tcgagagaac | catctcaaaa | 1560 |
| cccaaagggt | cagtaagagc | tccacaggta | tatgtcttgc | ctccaccaga | agaagagatg | 1620 |
| actaagaaac | aggtcactct | gacctgcatg | gtcacagact | tcatgcctga | agacatttac | 1680 |
| gtggagtgga | ccaacaacgg | gaaaacagag | ctaaactaca | agaacactga | accagtcctg | 1740 |

-continued

```
gactctgatg gttcttactt catgtacagc aagctgagag tggaaaagaa gaactgggtg    1800
gaaagaaata gctactcctg ttcagtggtc cacgagggtc tgcacaatca ccacacgact    1860
aagagcttct cccggactcc gggtaaatga taaccggtc                           1899

<210> SEQ ID NO 10
<211> LENGTH: 35
<212> TYPE: DNA
<213> ORGANISM: Artificial
<220> FEATURE:
<223> OTHER INFORMATION: Primer

<400> SEQUENCE: 10
gggatattgc tagcgccacc atggagaccc aaatg                                35

<210> SEQ ID NO 11
<211> LENGTH: 43
<212> TYPE: DNA
<213> ORGANISM: Artificial
<220> FEATURE:
<223> OTHER INFORMATION: Primer

<400> SEQUENCE: 11
tatctagacc ggttatcatt tacccggagt ccgggagaag ctc                       43

<210> SEQ ID NO 12
<211> LENGTH: 43
<212> TYPE: DNA
<213> ORGANISM: Artificial
<220> FEATURE:
<223> OTHER INFORMATION: Primer

<400> SEQUENCE: 12
agctcttcac cccccagagg gcccacaatc aagccctgtc ctc                       43

<210> SEQ ID NO 13
<211> LENGTH: 34
<212> TYPE: DNA
<213> ORGANISM: Artificial
<220> FEATURE:
<223> OTHER INFORMATION: Primer

<400> SEQUENCE: 13
ggccctctgg ggggtgaaga gctgcccatg ctgg                                 34
```